United States Patent
Van Sint Fiet et al.

(10) Patent No.: US 12,398,393 B2
(45) Date of Patent: Aug. 26, 2025

(54) RNA-EDITING OLIGONUCLEOTIDES FOR THE TREATMENT OF USHER SYNDROME

(71) Applicant: ProQR Therapeutics II B.V., Leiden (NL)

(72) Inventors: Lenka Van Sint Fiet, Leiden (NL); Kalyana Chakravarthi Dulla, Leiden (NL); Jim Swildens, Leiden (NL)

(73) Assignee: ProQR Therapeutics II B.V., Leiden (NL)

( * ) Notice: Subject to any disclaimer, the term of this patent is extended or adjusted under 35 U.S.C. 154(b) by 896 days.

(21) Appl. No.: 17/423,757

(22) PCT Filed: Jan. 27, 2020

(86) PCT No.: PCT/EP2020/051931
§ 371 (c)(1),
(2) Date: Jul. 16, 2021

(87) PCT Pub. No.: WO2020/157008
PCT Pub. Date: Aug. 6, 2020

(65) Prior Publication Data
US 2022/0112495 A1    Apr. 14, 2022

(30) Foreign Application Priority Data
Jan. 28, 2019 (EP) .................................... 19153895

(51) Int. Cl.
*C12N 15/113* (2010.01)
(52) U.S. Cl.
CPC ...... *C12N 15/113* (2013.01); *C12N 2310/315* (2013.01); *C12N 2310/322* (2013.01); *C12N 2310/531* (2013.01); *C12N 2320/34* (2013.01)
(58) Field of Classification Search
CPC .............. C12N 15/113; C12N 2310/11; C12N 2310/344; C12N 2310/533; C12N 2320/34; C12N 2310/315; C12N 2310/322; C12N 2310/531; C12Y 305/04004
See application file for complete search history.

(56) References Cited

U.S. PATENT DOCUMENTS

| 6,531,456 B1 | 3/2003 | Kurtzman et al. |
| 9,353,371 B2 | 5/2016 | Hastings et al. |

FOREIGN PATENT DOCUMENTS

| WO | WO 2012/168435 | 12/2012 |
| WO | WO 2013/036105 | 3/2013 |
| WO | WO 2015/004133 | 1/2015 |
| WO | WO 2016/005514 | 1/2016 |
| WO | WO 2016/034680 | 3/2016 |
| WO | WO 2016/097212 | 6/2016 |
| WO | WO 2016/135334 | 9/2016 |
| WO | WO 2016/138353 | 9/2016 |
| WO | WO 2017/060317 | 4/2017 |
| WO | WO 2017/186739 | 11/2017 |
| WO | WO 2017/220751 | 12/2017 |
| WO | WO 2018/041973 | 3/2018 |
| WO | WO 2018/055134 | 3/2018 |
| WO | WO 2018/109011 | 6/2018 |
| WO | WO 2018/134301 | 7/2018 |
| WO | WO 2018/189376 | 10/2018 |
| WO | WO 2019/005884 | 1/2019 |

OTHER PUBLICATIONS

Bainbridge et al., "Effect of gene therapy on visual function in Leber's congenital amaurosis," N Engl J Med., May 22, 2008, 358(21):2231-2239.
Becker et al., "Acylsilanes in rhodium(III)-catalyzed directed aromatic C—H alkenylations and siloxycarbene reactions with C—C double bonds," Angewandte Chemie Int Ed., 2014, 53(1):269-271.
European Search Report in European Application No. 19153895.8, dated Jul. 26, 2019, 8 pages.
Fuster-Garcia et al., "USH2A Gene Editing Using the CRISPR System," Mol Ther Nucl Acids., Aug. 12, 2017, 8:529-541.
Hashimoto et al., "Lentiviral gene replacement therapy of retinas in a mouse model for Usher syndrome type 1B," Gene Ther., 2007, 14(7):584-594.
International Preliminary Report on Patentability in International Application No. PCT/EP2020/051931, dated Jul. 27, 2021, 8 pages.
International Search Report and Written Opinion in International Application No. PCT/EP2020/051931, dated Jul. 27, 2021, 16 pages.
Montiel-Gonzalez et al., "Correction of mutations within the cystic fibrosis transmembrane conductance regulator by site-directed RNA editing," PNAS., 2013, 110(45):18285-18290.
Schneider et al., "Optimal guideRNAs for re-directing deaminase activity of hADAR1 and hADAR2 in trans," Nucleic Acids Res., 2014, 42(10):e87.
Stefl et al., "Structure and specific RNA binding of ADAR2 double-stranded RNA binding motifs," Structure, 2006, 14(2):345-355.
Tian et al., "A structural determinant required for RNA editing," Nucleic Acids Res., 2011, 39(13):5669-5681.
Van Wijk et al., "Identification of 51 Novel Exons of the Usher Syndrome Type 2A (USH2A) Gene That Encode Multiple Conserved Functional Domains and That Are Mutated in Patients with Usher Syndrome Type II," Am J Hum Genet., 2004, 74:738-744.
Woolf et al., "Toward the therapeutic editing of mutated RNA sequences," Proc Natl Acad Sci USA., 1995, 92:8298-8302.

*Primary Examiner* — Abigail Vanhorn
*Assistant Examiner* — Stephanie L Sullivan
(74) *Attorney, Agent, or Firm* — Fish & Richardson P.C.

(57) ABSTRACT

The invention relates to RNA editing oligonucleotides that are capable of bringing about specific editing of a target nucleotide (adenosine) in a target RNA molecule in a eukaryotic cell, wherein said oligonucleotide is for use in the treatment of Usher syndrome, and more preferably for the deamination of target adenosines that are part of a premature stop codon present in the USH2A pre-mRNA or USH2A mRNA.

15 Claims, 5 Drawing Sheets
Specification includes a Sequence Listing.

Fig. 1

GGCTAGAGTACT*TAATACGACTCACTATAGG*CTAGCCTCGAGAATTCcggaggtcaacaacg
agtcttttgtcatctacatgttcgtggtccacttcaccatccccatgattatcatcttttc
tgctatgggcagctcgtcttcaccgtcaaggag**ACGCCCTGCTGGCATTGAAGAGGAGTCTG
TTTTATTTGTCTGGTCAGAAGGAGCCCTTGAATTTATGGATGAAGGAGACACCCTGAGGCCT
TTCACACTCTACGAATATCGGGTCAGAGCCTGTAACTCCAAGGGTTCAGTGGAGAGTCTGTA
GTCATTAACACAAACTCTGGAAGCTCCACCTCAAGATTTTCCAGCTCCTTGGGCTCAAGCCA
CGAGTGCTCATTCAGTTCTGTTGAATTGGACAAAGCCAGAATCTCCCAATGGCATTATCTCC
CATTACCGTGTGGTCTACCAGGAGAGACCCGACGATCCTACATTTAACAGCCCTACCGTGCA
TGCTTTCACAGTGAAG**ttccggaactgc*atgctcaccaccatctgct*gcggcaagaacccac
tgggtgacgatgaggcctctgctaccgtgtccaagacggagacgagccaggtggccccggcc
taagacctgcctaggactctgtggccgactataggcgtctcccatccctacacctgtcgac
CCGGGCGGCCGCTTCCCTT

Fig. 2

ACGCCCTGCTGGCATTGAAGAGGAGTCTGTTTTATTTGTCTGGTCAGAAGGAGCCCTTGAAT
TTATGGATGAAGGAGACACCCTGAGGCCTTTCACACTCTACGAATATCGGGTCAGAGCCTGT
AACTCCAAGGGTTCAGTGGAGAGTCTGTAGTCATTAACACAAACTCTGGAAGCTCCACCTCA
AGATTTTCCAGCTCCTTGGGCTCAAGCCACGAGTGCTCATTCAGTTCTGTTGAATTGGACAA
AGCCAGAATCTCCCAATGGCATTATCTCCATTACCGTGTGGTCTACCAGGAGAGACCCGAC
GATCCTACATTTAACAGCCCTACCGTGCATGCTTTCACAGTGAAG

Fig. 3

```
                          A
5'-GGGUUCAGUGGAGAGUCUGU GUCAUUAACACAAACUCUGGAAGCUCCACCUCAAGAUUUUCCA-3'
       3'-tccucucagacA cgguaauuguguuugagaccuucgag-5'  (hUsh2a-1)
                     C
```

```
                          A
5'-GGGUUCAGUGGAGAGUCUGU GUCAUUAACACAAACUCUGGAAGCUCCACCUCAAGAUUUUCCA-3'
       3'-tccucucagacA cgguaauuguguuugagaccuucgagt-5'  (hUsh2a-2)
                     C
```

```
                          A
5'-GGGUUCAGUGGAGAGUCUGU GUCAUUAACACAAACUCUGGAAGCUCCACCUCAAGAUUUUCCA-3'
       3'-cuucuuagauA cgguaauuguguuugagaccuucgag-5'  (hUsh2a-3)
                    C
```

```
                          A
5' GGGUUCAGUGGAGAGUCUGU GUCAUUAACACAAACUCUGGAAGCUCCACCUCAAGAUUUUCCA 3'
       3'-ccucucagacA cgguaauugugguugcgaccuucgag 5'  (hUsh2a-4)
                    C
```

```
                          A
5' GGGUUCAGUGGAGAGUCUGU GUCAUUAACACAAACUCUGGAAGCUCCACCUCAAGAUUUUCCA 3'
       3'-ccucucagacA cgguaaugguguuugagaccuucgag-5'  (hUsh2a-5)
                    C
```

Fig. 4
A  hUsh2a-1
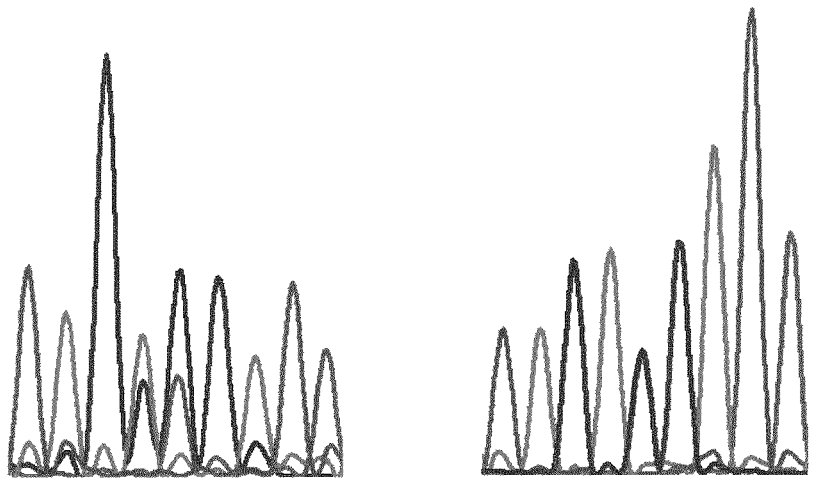
CTGTAGTCA
     G
(Fwd) – 66% editing
CTGTAGTCA
     G
(Rev) – 50% editing
B  hUsh2a-2
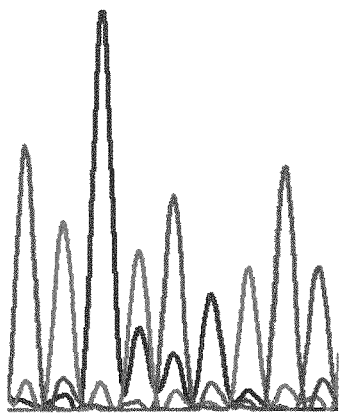
CTGTAGTCA
     G
(Fwd) – 21% editing
CTGTAGTCA
     G
(Rev) – 12% editing Fig. 4
C  hUsh2a-3
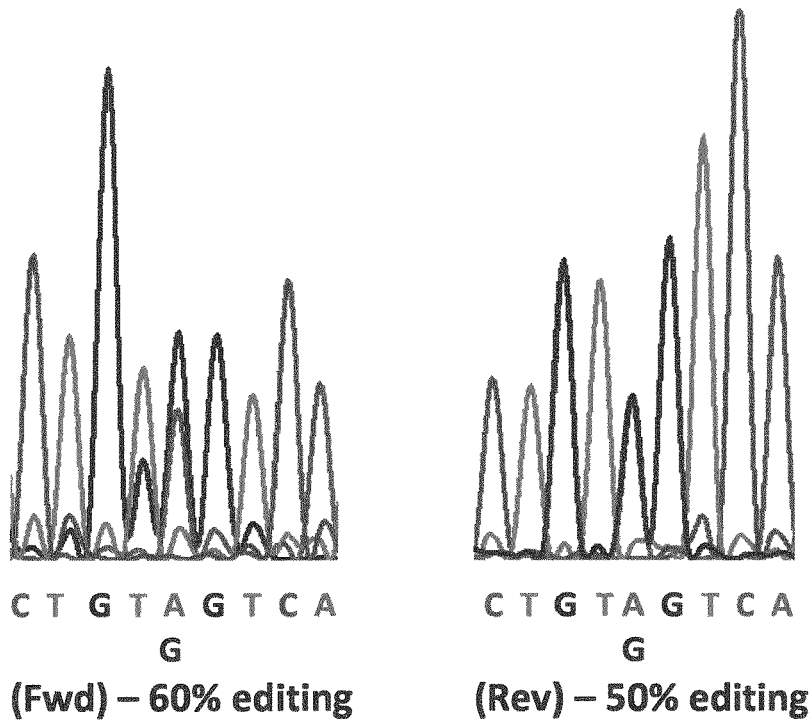
CTGTAGTCA
   G
(Fwd) – 60% editing
CTGTAGTCA
   G
(Rev) – 50% editing
D  hUsh2a-4
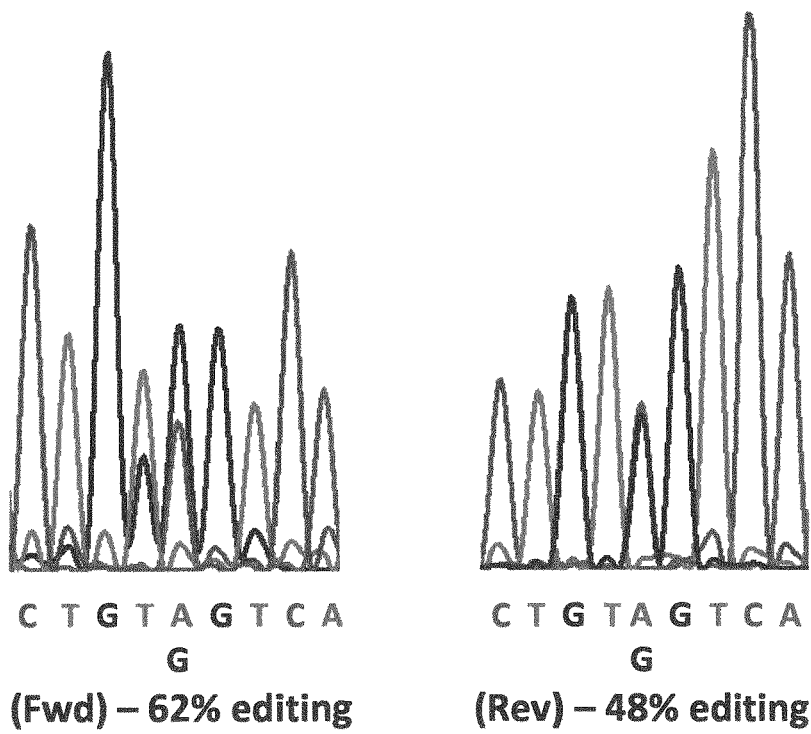
CTGTAGTCA
   G
(Fwd) – 62% editing
CTGTAGTCA
   G
(Rev) – 48% editing

Fig. 4
E  hUsh2a-5
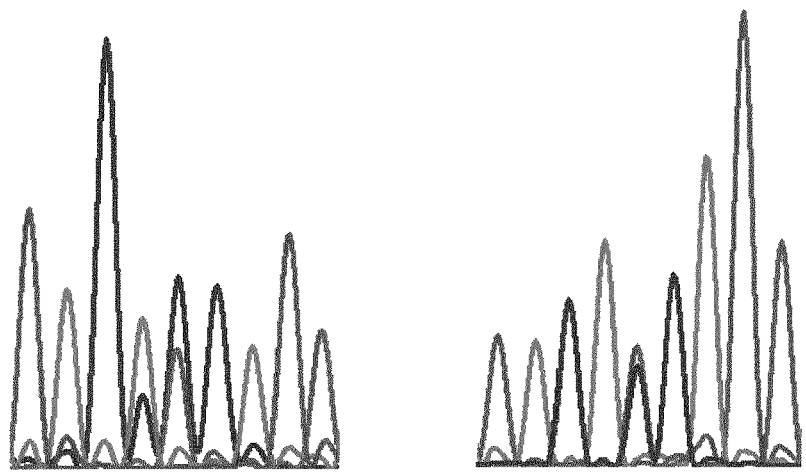
C T G T A G T C A
     G
(Fwd) – 62% editing
C T G T A G T C A
     G
(Rev) – 45% editing
F  No EON
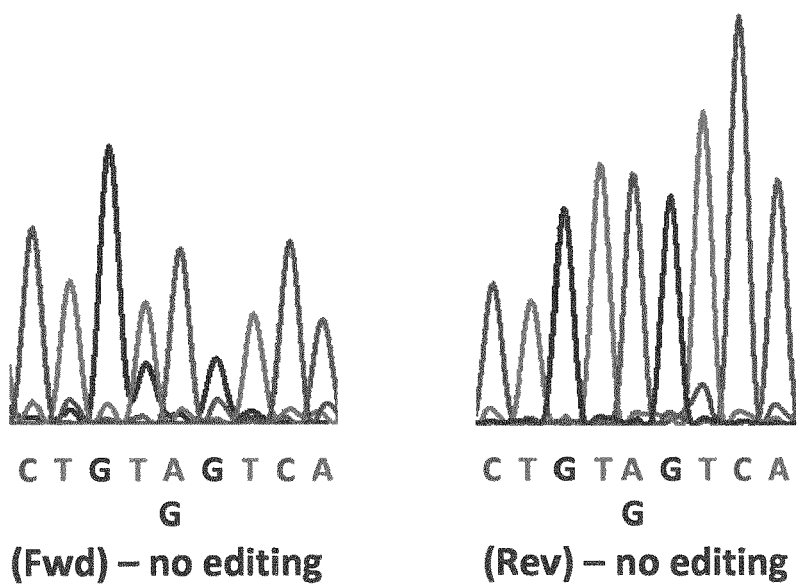
C T G T A G T C A
     G
(Fwd) – no editing
C T G T A G T C A
     G
(Rev) – no editing

RNA-EDITING OLIGONUCLEOTIDES FOR THE TREATMENT OF USHER SYNDROME

CROSS-REFERENCE TO RELATED APPLICATIONS

This application is a U.S. National Stage Application under 35 U.S.C. § 371 and claims the benefit of International Patent Application No. PCT/EP2020/051931, filed on Jan. 27, 2020, which claims the benefit of priority to EP Patent Application No. 19153895.8, filed on Jan. 28, 2019; the disclosures of the foregoing are incorporated herein by reference in their entirety.

SEQUENCE LISTING

This application contains a Sequence Listing that has been submitted electronically as an ASCII text file named 'Sequence_Listing.txt'. The ASCII text file, created on Jul. 16, 2021, is 4,0000 bytes in size. The material in the ASCII text file is hereby incorporated by reference in its entirety.

FIELD OF THE INVENTION

The invention relates to the field of medicine. In particular, it relates to the field of eye diseases, and more in particular to eye diseases caused by genetic defects, such as Usher syndrome. The invention involves the use of RNA editing technology in targeting (pre-) mRNA to deaminate target adenosines present in the target RNA and convert these to inosines using RNA editing antisense oligonucleotides.

BACKGROUND OF THE INVENTION

Usher syndrome (USH, or just 'Usher') and non-syndromic retinitis pigmentosa (NSRP) are degenerative diseases of the retina. Usher is clinically and genetically heterogeneous and by far the most common type of inherited deaf-blindness in man, with an estimated incidence of 1 in 6,000 individuals. The hearing impairment in Usher patients is mostly stable and congenital and can be partly compensated by hearing aids or cochlear implants. NSRP is more prevalent than Usher, occurring in 1 per 4,000 individuals. The degeneration of photoreceptor cells in Usher and NSRP is progressive and often leads to complete blindness between the third and fourth decade of life, thereby leaving time for therapeutic intervention.

Mutations in the USH2A gene are the most frequent cause of Usher explaining up to 50% of all Usher patients worldwide and also the most prevalent cause of NSRP in the USA, likely accounting for 12-25% of all cases of retinitis pigmentosa. The mutations are spread throughout the 72 USH2A exons and their flanking intronic sequences, and consist of nonsense and missense mutations, deletions, duplications, large rearrangements, and splicing variants. Exon 13 is by far the most frequently mutated exon including two founder mutations (c.2299delG (p.E767SfsX21) in USH2 patients and c.2276G>T (p.C759F) in NSRP patients). The c.2299delG mutation results in a frameshift causing a premature termination codon and is presumed to lead to nonsense mediated decay. For exon 50, fifteen pathogenic mutations have been reported, of which at least eight are clearly protein truncating. A mutation in intron 40 of USH2A (c.7595-2144A>G) creates a cryptic high-quality splice donor site in intron 40 resulting in the inclusion of an aberrant exon of 152 bp (pseudo exon 40, or PE40) in the mutant USH2A mRNA, and causes premature termination of translation.

Usher and other retinal dystrophies have for long been considered as incurable disorders. Several phase I/II clinical trials using gene augmentation therapy have led to promising results in selected groups of LCA/RP/USH patients with mutations in the RPE65 (Bainbridge et al. 2008. *Effect of gene therapy on visual function in Leber's congenital amaurosis*. N Engl J Med 358, 2231-2239) and MYO7A (Hashimoto et al. 2007. *Lentiviral gene replacement therapy of retinas in a mouse model for Usher syndrome type 1B*. Gene Ther 14(7):584-594) genes. Unfortunately, the size of the coding sequence (15,606 bp) and alternative splicing of the USH2A gene and mRNA, respectively hamper gene augmentation therapy due to the currently limiting cargo size of many available vectors (such as adeno-associated virus (AAV) and lentiviral vectors).

One approach to treat Usher caused by mutations in USH2A involves the use of antisense oligonucleotides (AONs) to influence splicing. Through this, mutated exons can be skipped from the (pre-) mRNA, thereby removing the mutated exon from the resulting mRNA. AONs are generally small polynucleotide molecules (16- to 25-mers) that are able to interfere with splicing as their sequence is complementary to that of target pre-mRNA molecules. The envisioned mechanism is such that upon binding of an AON to a target sequence, with which it is complementary, the targeted region within the pre-mRNA is no longer available for splicing factors which in turn results in skipping of the targeted exon. Therapeutically, this methodology can be used in two ways: a) to redirect normal splicing of genes in which mutations activate cryptic splice sites (such as with PE40, see above) and b) to skip exons that carry mutations in such a way, that the reading frame of the mRNA remains intact and a functional or partly functional protein is made (such as with exon 13, see above). For the USH2A gene, 28 out of the 72 described exons can potentially be skipped without disturbing the overall reading frame of the transcript. WO2016/005514 discloses exon skipping AONs for the USH2A pre-mRNA, directed at skipping of exon 13, exon 50 and PE40, and/or retaining exon 12. As disclosed therein, several AONs can be used for skipping exon 13. WO2018/055134 discloses further improved AONs for skipping exon 13 from USH2A pre-mRNA, and clinical trials are being planned in 2019 to treat Usher patients carrying mutations in exon 13 using one of the disclosed AONs. WO2017/186739 discloses AONs for the prevention of PE40 inclusion.

As mentioned above, 28 out of 72 exons in the USH2A transcript are in-frame, meaning that when they would be skipped, the neighboring exons—when linked—would be still in-frame and would result in a protein only lacking the translated region of the skipped exon. Subsequent data has to be generated to see if the resulting protein (in each instance of skipping the in-frame exon) maintains (a partial) function of the wild type usherin protein. 44 exons in the USH2A gene are not in-frame. Many of these exons, for which exon skipping is generally not considered as an option, also carry pathogenic mutations, but no treatments have yet been developed for patients suffering from Usher caused by defects in any of these particular exons.

SUMMARY OF THE INVENTION

The present invention relates to an RNA editing oligonucleotide (EON) capable of forming a double stranded complex with a target RNA molecule, wherein the EON when complexed with the target RNA molecule, and further complexed with an Adenosine Deaminase acting on RNA (ADAR), is capable of deaminating a target adenosine in the target RNA molecule, wherein the EON comprises a Central Triplet of three sequential nucleotides, wherein the nucleotide directly opposite the target adenosine is the middle nucleotide of the Central Triplet, and wherein the target RNA molecule is a human USH2A pre-mRNA or mRNA, or a part thereof. Preferably, the middle nucleotide of the Central Triplet is a cytidine. Preferably, one, two or three nucleotides in the Central Triplet comprise a modification, with the proviso that the middle nucleotide does not have a 2'-OMe modification in the sugar moiety. The invention also relates to an EON according to the invention, wherein the EON comprises at least one non-naturally occurring internucleoside linkage modification such as a phosphorothioate linkage. In a preferred embodiment, the invention relates to an EON according to the invention, wherein the target adenosine is part of a premature stop codon in the human USH2A pre-mRNA or mRNA, preferably wherein the premature stop codon is caused by the c.11864G>A mutation in exon 61 of the USH2A gene. In a further preferred embodiment, the EON according to the invention comprises or consists of the sequence selected from the group consisting of: SEQ ID NO:1, 2, 3, 4, and 5.

In another embodiment, the invention relates to a pharmaceutical composition comprising an EON according to the invention, and a pharmaceutically acceptable carrier. In yet another embodiment, the invention relates to an EON according to the invention for use in the treatment of Usher syndrome. In another embodiment, the invention relates to a use of the EON according to the invention in the manufacture of a medicament for the treatment of Usher syndrome.

In yet another embodiment, the invention relates to a method for the deamination of at least one specific target adenosine present in a target RNA molecule in a cell, wherein the target RNA molecule is a human USH2A pre-mRNA or mRNA, or a part thereof, the method comprising the steps of: providing the cell with an EON according to the invention; allowing uptake by the cell of the EON; allowing annealing of the EON to the target RNA molecule; allowing a mammalian ADAR enzyme comprising a natural dsRNA binding domain as found in the wild type enzyme to deaminate the target adenosine in the target RNA molecule to an inosine; and optionally identifying the presence of the inosine in the target RNA molecule, wherein the identification may be by: sequencing the target RNA molecule; assessing the presence of a functional, elongated, full length and/or wild type usherin protein when the target adenosine is located in a UGA or UAG stop codon, which is edited to a UGG codon through the deamination; assessing whether splicing of the pre-mRNA was altered by the deamination; or using a functional read-out, wherein the target RNA after the deamination encodes a functional, full length, elongated and/or wild type usherin protein.

BRIEF DESCRIPTION OF THE DRAWINGS

FIG. 1 shows the G-block sequence (5' to 3'; SEQ ID NO:6) to generate mutated exon 61 PCR product and RNA. The 355 bp sequence of exon 61 is in bold and upper case, with the c.11864G>A mutation underlined. The positions of the PCR primers are Italic. The 5' from exon 61 located RHO exon3 sequence and the 3' from exon 61 located RHO exon5 sequences are in lower case.

FIG. 2 shows only the 355 bp DNA sequence of the mutated exon 61 (SEQ ID NO:7) of the human USH2A gene. The c.11864G>A mutation is underlined.

FIG. 3 shows the details of the five initially designed RNA editing oligonucleotides (hUsh2a1 to 5) targeting the adenosine of the c.11864G>A mutation in exon 61 of human USH2A RNA. In each of the five panels the upper strand represents from 5' to 3' part (SEQ ID NO:10) a part of exon 61 RNA including the mutation (popped-out). The five EONs are displayed from 3' to 5' (5' to 3' sequences are SEQ ID NO:1 to 5, respectively). The 3' T in hUsh2a-1 and the 3' T in hUsh2a-2 are inverted deoxythymidine residues. The 5' T in hUsh2a-2 is an inverted dideoxythymidine residue. The ultimate five nucleotides in each of the five EONs at both the 5' and 3' ends (deoxyT and dideoxyT not included) are connected by phosphorothioated linkages. Lower case in the EONs represents RNA with 2'-OMe modifications, but bold lower case in the EONs represent RNA with 2'-MOE modifications. Bold upper case in the EONs represent DNA. Hence, the C (popping out) opposite the target adenosine (A) is DNA as well as its neighboring 3' A in each of the five EONs. Underlined sequences (in both target as EON) represent GU wobble base pairs, GA mismatches and CU mismatches.

FIG. 4 shows the sequence data upon RNA editing of the target adenosine present in the premature stop codon caused by the c.11864G>A mutation in exon 61 of the USH2A gene, after using an in vitro generated exon 61 target molecule, purified ADAR and five EONs as disclosed in the examples. The sequence was generated using a forward (Fwd) and a Reverse (Rev) primer. Panels (A-B) shows the results with EONs hUsh2a-1 (A)and hUsh2a-2(B). Panels (C-D) shows the results with EONs hUsh2a-3 (c) and hUsh2a-4(D). Panels (E-F) shows the results with EON hUsh2a-5 (E) and a negative control in which no EON (F) was used. The percentage editing was calculated by the taking the ratio between the A peak (mutant) and G peak (edited) at the position given by an A and a G. The target sequence is the same for each panel (SEQ ID NO:13).

DETAILED DESCRIPTION OF THE INVENTION

The inventors of the present invention have sought for other means to correct defects in the exons within USH2A. The inventors have used another type of RNA repair, often referred to as 'RNA editing'. RNA editing is a natural process through which eukaryotic cells alter the sequence of their RNA molecules, often in a site-specific and precise way, thereby increasing the repertoire of genome encoded RNAs by several orders of magnitude. RNA editing enzymes have been described for eukaryotic species throughout the animal and plant kingdoms, and these processes play an important role in managing cellular homeostasis in metazoans from the simplest life forms such as *Caenorhabditis elegans*, to humans. Examples of RNA editing are adenosine (A) to inosine (I) and cytidine (C) to uridine (U) conversions through enzymes called adenosine deaminase and cytidine deaminase, respectively. The most extensively studied RNA editing system is the adenosine deaminase enzyme.

Adenosine deaminase is a multi-domain protein, comprising a recognition domain and a catalytic domain. The recognition domain recognizes a specific double-stranded RNA (dsRNA) sequence and/or conformation, whereas the catalytic domain converts an adenosine into an inosine in a nearby, more or less predefined, position in the target RNA, by deamination of the nucleobase. Inosine is read as guanosine by the translational machinery of the cell, meaning that, if an edited adenosine is in a coding region of an mRNA or pre-mRNA, it can recode the protein sequence. Adenosine deaminases are part of a family of enzymes referred to as Adenosine Deaminases acting on RNA (ADAR), including human deaminases hADAR1, hADAR2 and hADAR3.

The use of oligonucleotides to edit a target RNA applying adenosine deaminase is known in the art. Montiel-Gonzalez et al. (PNAS 2013, 110(45):18285-18290) described the editing of a target RNA using a genetically engineered fusion protein, comprising an adenosine deaminase domain of the hADAR2 protein, fused to a bacteriophage lambda N protein, which recognises the boxB RNA hairpin sequence. A disadvantage of this method in a therapeutic setting is the need for the fusion protein. It requires cells to be either transduced with the fusion protein, which is a major hurdle, or that target cells are transfected with a nucleic acid construct encoding the engineered adenosine deaminase fusion protein for expression. Vogel et al. (2014. Angewandte Chemie Int Ed 53:267-271) disclosed editing of RNA coding for eCFP and Factor V Leiden, using a benzylguanosine substituted guide RNA and a genetically engineered fusion protein, comprising the adenosine deaminase domains of ADAR1 or 2 (lacking the dsRNA binding domains) genetically fused to a SNAP-tag domain (an engineered 06-alkylguanosine-DNA-alkyl transferase). This system suffers from similar drawbacks as the genetically engineered ADARs described by Montiel-Gonzalez et al. (2013). Woolf et al. (1995. Proc Natl Acad Sci USA 92:8298-8302) disclosed a simpler approach, using relatively long single-stranded antisense RNA oligonucleotides (25-52 nucleotides in length) wherein the longer oligonucleotides (34-mer and 52mer) could promote editing of the target RNA by endogenous ADAR because of the double-stranded nature of the target RNA and the hybridizing oligonucleotide, but only appeared to function in cell extracts or in amphibian (*Xenopus*) oocytes by microinjection, and suffered from severe lack of specificity: nearly all adenosines in the target RNA strand that was complementary to the antisense oligonucleotide were edited. Woolf et al. (1995) did not achieve deamination of a specific target adenosine in the target RNA sequence, because nearly all adenosines opposite an unmodified nucleotide in the antisense oligonucleotide were edited through a process sometimes referred to as 'promiscuous editing'. WO2016/097212 discloses RNA editing oligonucleotides, characterized by a sequence that is complementary to a target RNA sequence ('targeting portion') and by the presence of a stem-loop structure ('recruitment portion'). WO2017/220751 discloses RNA editing oligonucleotides without a recruitment portion, but with a strand of nucleotides that are complementary to a target region, for the specific editing of a single adenosine, and wherein the oligonucleotide comprises one or more mismatches, wobbles and/or bulges in combination with specific chemical modifications. Very specific locations of specific chemical modifications in such RNA editing oligonucleotides were further disclosed in WO2018/041973.

Most of the RNA editing prior art relates to the general applicability of this phenomenon for any type of disease or genetic disorder in which a specific target adenosine should be edited to an inosine to restore translation (where the adenosine was part of a stop codon), and/or to repair the RNA when the adenosine was part of a codon that altered the protein and caused the genetic disease. The documents in the prior art did not specifically reveal the application of RNA editing oligonucleotides in eye diseases such as Usher syndrome, in which genetic alterations are the cause of the disorder, or how this specifically should be performed. In contrast, a lot of prior art has accumulated that reveals the usefulness of antisense oligonucleotides in downregulating protein expression, or that influence splicing (e.g. see WO2012/168435, WO2013/036105, WO2016/005514, WO2016/034680, WO2016/138353, WO2016/135334, WO2017/060317, WO2017/186739, WO2018/055134, WO2015/004133, WO2018/189376, WO2018/109011, and U.S. Pat. No. 9,353,371). To the best of the knowledge of the inventors of the present invention RNA editing oligonucleotides have not been used to deaminate specific adenosines in genes causing eye defects, and applying such RNA editing oligonucleotides in the treatment of eye disorders.

The present invention relates to RNA editing oligonucleotides (herein generally abbreviated to "EONs") and their use in the treatment of eye disease, particularly Usher syndrome. The EONs of the present invention target specific adenosines in the USH2A pre-mRNA or mRNA and deaminate these to inosines, read as guanosines in translation. It is noted that the adenosine (A) itself does not have to be the mutation causing Usher syndrome, but may for instance be part of a premature termination codon that is the cause of the disease (since, for instance a shorter usherin protein product is produced), and in which for instance the guanosine (G) or the thymidine (T) is the real mutation. Repairing the adenosine to an inosine may result in a wild type protein, or in a protein with an altered amino acid instead of the stop codon (and altered in respect of the original codon of the wild type mRNA), but should allow continued translation.

An EON of the present invention does not comprise a recruitment portion as described in WO2016/097212. The EONs of the present invention do also not comprise a portion that can form an intramolecular stem-loop structure, such as the oligonucleotides used in CRISPR/CAS systems (e.g. WO2019/005884). The EONs of the present invention are not (covalently) linked to an enzyme that can deaminate a target nucleotide before it enters a target cell, but can form a complex with such an enzymatic entity (preferably ADAR) present in a target cell (hence, recruiting, interacting and complexing with an endogenous ADAR enzyme). The EONs of the present invention are shorter than such oligonucleotides from the art, which makes them cheaper to produce, easier to use and easier to manufacture. WO2017/220751 and WO2018/041973 disclose EONs that are complementary to a target RNA for deaminating a target adenosine present in a target RNA sequence to which the EON is complementary, but also lacked a recruitment portion while still being capable of harnessing ADAR enzymes present in the cell to edit the target adenosine. The present invention makes use of that knowledge and aims to solve the problem of targeting Usher syndrome mutations for which exon skipping is not the preferred therapeutic option, or where an alternative approach would be sought.

The skilled person knows that an oligonucleotide, such as an RNA oligonucleotide, generally consists of repeating monomers. Such a monomer is most often a nucleotide or a nucleotide analogue. The most common naturally occurring nucleotides in RNA are adenosine monophosphate (A), cytidine monophosphate (C), guanosine monophosphate (G), and uridine monophosphate (U). These consist of a pentose sugar, a ribose, a 5'-linked phosphate group which is linked via a phosphate ester, and a 1'-linked base. The sugar connects the base and the phosphate and is therefore often referred to as the "scaffold" of the nucleotide. A modification in the pentose sugar is therefore often referred to as a "scaffold modification". For severe modifications, the original pentose sugar might be replaced in its entirety by another moiety that similarly connects the base and the phosphate. It is therefore understood that while a pentose sugar is often a scaffold, a scaffold is not necessarily a pentose sugar.

A base, sometimes called a nucleobase, is generally adenine, cytosine, guanine, thymine or uracil, or a derivative thereof. Cytosine, thymine and uracil are pyrimidine bases, and are generally linked to the scaffold through their 1-nitrogen. Adenine and guanine are purine bases and are generally linked to the scaffold through their 9-nitrogen.

A nucleotide is generally connected to neighboring nucleotides through condensation of its 5'-phosphate moiety to the 3'-hydroxyl moiety of the neighboring nucleotide monomer. Similarly, its 3'-hydroxyl moiety is generally connected to the 5'-phosphate of a neighboring nucleotide monomer. This forms phosphodiester bonds. The phosphodiesters and the scaffold form an alternating copolymer. The bases are grafted on this copolymer, namely to the scaffold moieties. Because of this characteristic, the alternating copolymer formed by linked monomers of an oligonucleotide is often called the "backbone" of the oligonucleotide. Because phosphodiester bonds connect neighboring monomers together, they are often referred to as "backbone linkages". It is understood that when a phosphate group is modified so that it is instead an analogous moiety such as a phosphorothioate, such a moiety is still referred to as the backbone linkage of the monomer. This is referred to as a "backbone linkage modification". In general terms, the backbone of an oligonucleotide comprises alternating scaffolds and backbone linkages.

In one aspect, the nucleobase in an EON of the present invention is adenine, cytosine, guanine, thymine, or uracil. In another aspect, the nucleobase is a modified form of adenine, cytosine, guanine, or uracil. In another aspect, the modified nucleobase is hypoxanthine (the nucleobase in inosine), pseudouracil, pseudocytosine, 1-methylpseudouracil, orotic acid, agmatidine, lysidine, 2-thiouracil, 2-thiothymine, 5-halouracil, 5-halomethyluracil, 5-trifluoromethyluracil, 5-propynyluracil, 5-propynylcytosine, 5-aminomethyluracil, 5-hydroxymethyluracil, 5-formyluracil, 5-aminomethylcytosine, 5-formylcytosine, 5-hydroxymethylcytosine, 7-deazaguanine, 7-deazaadenine, 7-deaza-2,6-diaminopurine, 8-aza-7-deazaguanine, 8-aza-7-deazaadenine, 8-aza-7-deaza-2,6-diaminopurine, pseudoisocytosine, N4-ethylcytosine, N2-cyclopentylguanine, N2-cyclopentyl-2-aminopurine, N2-propyl-2-aminopurine, 2,6-diaminopurine, 2-aminopurine, G-clamp, Super A, Super T, Super G, amino-modified nucleobases or derivatives thereof; and degenerate or universal bases, like 2,6-difluorotoluene, or absent like abasic sites (e.g. 1-deoxyribose, 1,2-dideoxyribose, 1-deoxy-2-O-methylribose, azaribose). The terms 'adenine', 'guanine', 'cytosine', 'thymine', 'uracil' and 'hypoxanthine' as used herein refer to the nucleobases as such. The terms 'adenosine', 'guanosine', 'cytidine', 'thymidine', 'uridine' and 'inosine' refer to the nucleobases linked to the (deoxy)ribosyl sugar. The term 'nucleoside' refers to the nucleobase linked to the (deoxy) ribosyl sugar. The term 'nucleotide' refers to the respective nucleobase-(deoxy)ribosyl-phospholinker, as well as any chemical modifications of the ribose moiety or the phospho group. Thus the term would include a nucleotide including a locked ribosyl moiety (comprising a 2'-4' bridge, comprising a methylene group or any other group, well known in the art), a nucleotide including a linker comprising a phosphodiester, phosphotriester, phosphoro(di)thioate, methylphosphonates, phosphoramidate linkers, and the like. Sometimes the terms adenosine and adenine, guanosine and guanine, cytosine and cytidine, uracil and uridine, thymine and thymidine, inosine and hypoxanthine, are used interchangeably to refer to the corresponding nucleobase, nucleoside or nucleotide. Sometimes the terms nucleobase, nucleoside and nucleotide are used interchangeably, unless the context clearly requires differently.

Whenever reference is made to an 'antisense oligonucleotide' ('AON'), an 'RNA editing oligonucleotide' ('EON'), an 'oligonucleotide', or an 'oligo' then both oligoribonucleotides and deoxyoligoribonucleotides are meant unless the context dictates otherwise. Whenever reference is made to an 'oligoribonucleotide' it may comprise the ribonucleosides adenosine (A), guanosine (G), cytidine (C), 5-methylcytidine ($m^5C$), uridine (U), 5-methyluridine ($m^5U$) or inosine (I). Whenever reference is made to a 'deoxyoligoribonucleotide' it may comprise the deoxyribonucleosides deoxyadenosine (A), deoxyguanosine (G), deoxycytidine (C), thymine (T) or deoxyinosine (I). In a preferred aspect, the EON of the present invention is mostly an oligoribonucleotide that may comprise chemical modifications and, at a few specified positions, deoxyribonucleosides (DNA). When reference is made to nucleotides in the oligonucleotide construct, such as cytosine, then 5-methylcytosine, 5-hydroxymethylcytosine, Pyrrolocytidine, and β-D-Glucosyl-5-hydroxy-methylcytosine are included. When reference is made to adenine, then 2-aminopurine, 2,6-diaminopurine, 3-deazaadenosine, 7-deazaadenosine, 8-azidoadenosine, 8-methyladenosine, 7-aminomethyl-7-deazaguanosine, 7-deazaguanosine, N6-Methyladenine and 7-methyladenine are included. When reference is made to uracil, then 5-methoxyuracil, 5-methyluracil, dihydrouracil, pseudouracil, and thienouracil, dihydrouracil, 4-thiouracil and 5-hydroxymethyluracil are included. When reference is made to guanosine, then 7-methylguanosine, 8-aza-7-deazaguanosine, thienoguanosine and 1-methylguanosine are included. When reference is made to nucleosides or nucleotides, then ribofuranose derivatives, such as 2'-deoxy, 2'-hydroxy, 2'-fluororibose and 2'-O-substituted variants, such as 2'-O-methyl, are included, as well as other modifications, including 2'-4' bridged variants. When reference is made to oligonucleotides, then linkages between two mono-nucleotides may be phosphodiester linkages as well as modifications thereof, including, phosphodiester, phosphotriester, phosphoro(di)thioate, methylphosphonate, phosphor-amidate linkers, and the like.

In one aspect, an EON of the present invention comprises a 2'-substituted phosphorothioate monomer, preferably a 2'-substituted phosphorothioate RNA monomer, a 2'-substituted phosphate RNA monomer, or comprises 2'-substituted mixed phosphate/phosphorothioate monomers. It is noted that DNA is considered as an RNA derivative in respect of 2' substitution. An EON of the present invention comprises at least one 2'-substituted RNA monomer connected through or linked by a phosphorothioate or phosphate backbone linkage, or a mixture thereof. The 2'-substituted RNA preferably is 2'-F, 2'-H (DNA), 2'-O-Methyl or 2'-O-(2-methoxyethyl). The 2'-O-Methyl is often abbreviated to "2'-OMe" and the 2'-O-(2-methoxyethyl) moiety is often abbreviated to "2'-MOE". More preferably, the 2'-substituted RNA monomer in the EON of the present invention is a 2'-OMe monomer, except for the monomer opposite the target adenosine, as further outlined herein, which should not carry a 2'-OMe substitution. In a preferred aspect of this aspect is provided an EON according to the invention, wherein the 2'-substituted monomer can be a 2'-substituted RNA monomer, such as a 2'-F monomer, a 2'-$NH_2$ monomer, a 2'-H monomer (DNA), a 2'-O-substituted monomer, a 2'-OMe monomer or a 2'-MOE monomer or mixtures thereof. Preferably, the monomer opposite the target adenosine is a 2'-H monomer (DNA) but may also be a monomer that allows deamination of the target adenosine, other than a 2'-OMe monomer. Preferably, any other 2'-substituted monomer within the EON is a 2'-substituted RNA monomer, such as a 2'-OMe RNA monomer or a 2'-MOE RNA monomer, which may also appear within the EON in combination.

Throughout the application, a 2'-OMe monomer within an EON of the present invention may be replaced by a 2'-OMe phosphorothioate RNA, a 2'-OMe phosphate RNA or a 2'-OMe phosphate/phosphorothioate RNA. Throughout the application, a 2'-MOE monomer may be replaced by a 2'-MOE phosphorothioate RNA, a 2'-MOE phosphate RNA or a 2'-MOE phosphate/phosphorothioate RNA. Throughout the application, an oligonucleotide consisting of 2'-OMe RNA monomers linked by or connected through phosphorothioate, phosphate or mixed phosphate/phosphorothioate backbone linkages may be replaced by an oligonucleotide consisting of 2'-OMe phosphorothioate RNA, 2'-OMe phosphate RNA or 2'-OMe phosphate/phosphorothioate RNA. Throughout the application, an oligonucleotide consisting of 2'-MOE RNA monomers linked by or connected through phosphorothioate, phosphate or mixed phosphate/phosphorothioate backbone linkages may be replaced by an oligonucleotide consisting of 2'-MOE phosphorothioate RNA, 2'-MOE phosphate RNA or 2'-MOE phosphate/phosphorothioate RNA.

In addition to the specific preferred chemical modifications at certain positions in compounds of the invention, compounds of the invention may comprise or consist of one or more (additional) modifications to the nucleobase, scaffold and/or backbone linkage, which may or may not be present in the same monomer, for instance at the 3' and/or 5' position. A scaffold modification indicates the presence of a modified version of the ribosyl moiety as naturally occurring in RNA (i.e. the pentose moiety), such as bicyclic sugars, tetrahydropyrans, hexoses, morpholinos, 2'-modified sugars, 4'-modified sugar, 5'-modified sugars and 4'-substituted sugars. Examples of suitable modifications include, but are not limited to 2'-O-modified RNA monomers, such as 2'-O-alkyl or 2'-O-(substituted)alkyl such as 2'-O-methyl, 2'-O-(2-cyanoethyl), 2'-MOE, 2'-O-(2-thiomethyl)ethyl, 2'-O-butyryl, 2'-O-propargyl, 2'-O-allyl, 2'-O-(2-aminopropyl), 2'-O-(2-(dimethylamino)propyl), 2'-O-(2-amino)ethyl, 2'-O-(2-(dimethylamino)ethyl); 2'-deoxy (DNA); 2'-0-(haloalkyl) methyl such as 2'-O-(2-chloroethoxy)methyl (MCEM), 2'-O-(2,2-dichloroethoxy)methyl (DCEM); 2'-O-alkoxycarbonyl such as 2'-O-[2-(methoxycarbonyl)ethyl](MOCE), 2'-O-[2-N-methylcarbamoyl)ethyl](MCE), 2'-O-[2-(N,N-dimethylcarbamoyl)ethyl](DCME); 2'-halo e.g. 2'-F, FANA; 2'-O-[2-(methylamino)-2-oxoethyl](NMA); a bicyclic or bridged nucleic acid (BNA) scaffold modification such as a conformationally restricted nucleotide (CRN) monomer, a locked nucleic acid (LNA) monomer, a xylo-LNA monomer, an α-LNA monomer, an α-L-LNA monomer, a β-D-LNA monomer, a 2'-amino-LNA monomer, a 2'-(alkylamino)-LNA monomer, a 2'-(acylamino)-LNA monomer, a 2'-N-substituted 2'-amino-LNA monomer, a 2'-thio-LNA monomer, a (2'-0,4'-C) constrained ethyl (cEt) BNA monomer, a (2'-0,4'-C) constrained methoxyethyl (cMOE) BNA monomer, a 2',4'-BNA$^{NC}$(NH) monomer, a 2',4'-BNA$^{NC}$(NMe) monomer, a 2',4'-BNA$^{N}$C(NBn) monomer, an ethylene-bridged nucleic acid (ENA) monomer, a carba-LNA (cLNA) monomer, a 3,4-dihydro-2H-pyran nucleic acid (DpNA) monomer, a 2'-C-bridged bicyclic nucleotide (CBBN) monomer, an oxo-CBBN monomer, a heterocyclic-bridged BNA monomer (such as triazolyl or tetrazolyl-linked), an amido-bridged BNA monomer (such as AmNA), an urea-bridged BNA monomer, a sulfonamide-bridged BNA monomer, a bicyclic carbocyclic nucleotide monomer, a TriNA monomer, an α-L-TriNA monomer, a bicyclo DNA (bcDNA) monomer, an F-bcDNA monomer, a tricyclo DNA (tcDNA) monomer, an F-tcDNA monomer, an alpha anomeric bicyclo DNA (abcDNA) monomer, an oxetane nucleotide monomer, a locked PMO monomer derived from 2'-amino LNA, a guanidine-bridged nucleic acid (GuNA) monomer, a spirocyclopropylene-bridged nucleic acid (scpBNA) monomer, and derivatives thereof; cyclohexenyl nucleic acid (CeNA) monomer, altriol nucleic acid (ANA) monomer, hexitol nucleic acid (HNA) monomer, fluorinated HNA (F-HNA) monomer, pyranosyl-RNA (p-RNA) monomer, 3'-deoxypyranosyl DNA (p-DNA), unlocked nucleic acid UNA); an inverted version of any of the monomers above. All these modifications are known to the person skilled in the art.

A "backbone modification" indicates the presence of a modified version of the ribosyl moiety ("scaffold modification"), as indicated above, and/or the presence of a modified version of the phosphodiester as naturally occurring in RNA ("backbone linkage modification"). Examples of internucleoside linkage modifications are phosphorothioate (PS), chirally pure phosphorothioate, Rp phosphorothioate, Sp phosphorothioate, phosphorodithioate (PS2), phosphonoacetate (PACE), thophosphonoacetate, phosphonacetamide (PACA), thiophosphonacetamide, phosphorothioate prodrug, S-alkylated phosphorothioate, H-phosphonate, methyl phosphonate, methyl phosphonothioate, methyl phosphate, methyl phosphorothioate, ethyl phosphate, ethyl phosphorothioate, boranophosphate, boranophosphorothioate, methyl boranophosphate, methyl boranophosphorothioate, methyl boranophosphonate, methyl boranophosphonothioate, phosphoryl guanidine (PGO), methylsulfonyl phosphoroamidate, phosphoramidite, phosphonamidite, N3'→P5' phosphoramidate, N3'→P5' thiophosphoramidate, phosphorodiamidate, phosphorothiodiamidate, sulfamate, dimethylenesulfoxide, sulfonate, triazole, oxalyl, carbamate, methyleneimino (MMI), and thioacetamido (TANA); and their derivatives.

EONs of the present invention do not include a 5'-terminal 06-benzylguanosine or a 5'-terminal amino modification and are not covalently linked to a SNAP-tag domain (an engineered 06-alkylguanosine-DNA-alkyl transferase). In one aspect, an EON of the present invention comprises 0, 1, 2 or 3 wobble base pairs with the target sequence, and/or 0, 1, 2, or 3 mismatches with the target RNA sequence, wherein a single mismatch may comprise multiple sequential nucleotides. Similarly, an EON of the present invention does not include a boxB RNA hairpin sequence. An EON according to the present invention can utilise endogenous cellular pathways and naturally available ADAR enzymes to specifically edit a target adenosine in a target RNA sequence. An EON of the invention is capable of recruiting ADAR and complex with it and then allow the deamination of a (single) specific target adenosine nucleotide in a target RNA sequence. Ideally, only one adenosine is deaminated. Alternatively, 1, 2, or 3 adenosine nucleotides are deaminated, for instance when target adenosines are in proximity of each other. For example, when the mutation is an alteration from a wild type GGA (glycine) codon to a mutant GAA (glutamic acid) codon, deamination of both adenosines would result in GGG, which also encodes a glycine. An EON of the invention, when complexed to ADAR, preferably deaminates a single target adenosine.

Analysis of natural targets of ADAR enzymes has indicated that these generally include mismatches between the two strands that form the RNA helix edited by ADAR1 or 2. It has been suggested that these mismatches enhance the specificity of the editing reaction (Stefl et al. 2006. *Structure* 14(2):345-355; Tian et al. 2011. *Nucleic Acids Res* 39(13): 5669-5681). Characterization of optimal patterns of paired/mismatched nucleotides between the EONs and the target RNA also appears crucial for development of efficient ADAR-based EON therapy.

An EON of the present invention makes use of specific nucleotide modifications at predefined spots to ensure stability as well as proper ADAR binding and activity. These changes may vary and may include modifications in the backbone of the EON, in the sugar moiety of the nucleotides as well as in the nucleobases or the phosphodiester linkages, as outlined in detail above. They may also be variably distributed throughout the sequence of the EON. Specific modifications may be needed to support interactions of different amino acid residues within the RNA-binding domains of ADAR enzymes, as well as those in the deaminase domain. For example, phosphorothioate linkages between nucleotides or 2'-OMe or 2'-MOE modifications may be tolerated in some parts of the EON, while in other parts they should be avoided so as not to disrupt crucial interactions of the enzyme with the phosphate and 2'-OH groups. Specific nucleotide modifications may also be necessary to enhance the editing activity on substrate RNAs where the target sequence is not optimal for ADAR editing. Previous work has established that certain sequence contexts are more amenable to editing. For example, the target sequence 5'-UAG-3' (with the target A in the middle) contains the most preferred nearest-neighbor nucleotides for ADAR2, whereas a 5'-CAA-3' target sequence is disfavored (Schneider et al. 2014. *Nucleic Acids Res* 42(10):e87). The structural analysis of ADAR2 deaminase domain hints at the possibility of enhancing editing by careful selection of the nucleotides that are opposite to the target trinucleotide. For example, the 5'-CAA-3' target sequence, paired to a 3'-GCU-5' sequence on the opposing strand (with the A-C mismatch formed in the middle), is disfavored because the guanosine base sterically clashes with an amino acid side chain of ADAR2.

An EON of the present invention comprises (when not expressed through a viral vector) one or more nucleotides with one or more sugar modifications. Thereby, a single nucleotide of the EON can have one, or more than one sugar modification. Within the EON, one or more nucleotide(s) can have such sugar modification(s). It is also an aspect of the invention that the nucleotide within the EON of the present invention that is opposite to the nucleotide that needs to be edited does not contain a 2'-OMe or a 2'-MOE modification. Often the nucleotides that are directly 3' and 5' of this nucleotide (the 'neighbouring nucleotides') in the EON also lack such a chemical modifications, although not both of the neighbouring nucleotides should not contain a 2'-O-alkyl group (such as a 2'-OMe). Either one, or both neighbouring nucleotides or all three nucleotides of the 'Central Triplet' may carry 2'-OH.

The 'Central Triplet' as used herein are the three nucleotides opposite the target adenosine in the target RNA, wherein the middle nucleotide in the Central Triplet is directly opposite the target adenosine. The Central Triplet does not have to be in the centre of the EON, as it may be located more to the 3' as well as to the 5' end of the EON, whatever is preferred for a certain target. The term 'Central' in this aspect has therefore more the meaning of the triplet that is in the centre of catalytic activity when it comes to chemical modifications and targeting the target adenosine. It should also be noted that the EONs are sometimes depicted from 3' to 5', especially when the target sequence is shown from 5' to 3'. However, whenever herein the order of nucleotides within the EON is discussed it is always from 5' to 3' of the EON. The position can also be expressed in terms of a particular nucleotide within the EON while still adhering to the 5' to 3' directionality, in which case other nucleotides 5' of the said nucleotide are marked as negative positions and those 3' of it as positive positions.

As outlined herein, the nucleotides outside the Central triplet are often 2'-OMe or 2'-MOE modified. However, this is not a strict requirement of the EONs of the present invention. The use of these 2' substitutions assures a proper stability of those parts of the EON, but other modifications may be applied as well.

The present invention relates to an EON comprising the sequence 'XYZ' as the Central Triplet, wherein X is the middle nucleotide opposite the target adenosine, the X may be cytidine, 5-methylcytidine, 5-hydroxymethylcytidine, uridine, or pyrrolocytidine, whereas the Y and/or Z may be inosine, 5-methylcytidine, pyrrolocytidine, pseudouridine, 4-thiouridine, thienouridine, 2-aminopurine, 2,6-diaminopurine, thienoguanosine, 5-methoxyuridine, dihydrouridine, 5-hydroxymethylcytidine, 5-methyluridine, 8-aza-7-deazaguanosine, 7-aminomethyl-7-deazaguanosine, 7-methyladenosine, 8-methyladenosine, 3-deazaadenosine, 7-deazaadenosine, 8-azidoadenosine, etc., depending on the nucleotides opposite the Central Triplet; hence depending on the target RNA sequence. Ergo, in a preferred aspect, said base modification is selected from the group consisting of 2-aminopurine, 2,6-diaminopurine, 3-deazaadenosine, 7-deazaadenosine, 7-methyladenosine, 8-azidoadenosine, 8-methyladenosine, 5-hydroxymethylcytidine, 5-methylcytidine, Pyrrolocytidine, 7-aminomethyl-7-deazaguanosine, 7-deazaguanosine, 7-methylguanosine, 8-aza-7-deazaguanosine, thienoguanosine, inosine, 4-thio-uridine, 5-methoxyuridine, 5-methyluridine, dihydrouridine, pseudouridine, and thienouridine.

In another preferred aspect, the sugar modification is selected from the group consisting of deoxyribose (i.e. DNA), Unlocked Nucleic Acid (UNA) and 2'-fluororibose. In a particularly preferred aspect, the present invention relates to an EON comprising a Central Triplet of 3 sequential nucleotides, wherein the nucleotide directly opposite the target adenosine is the middle nucleotide of the Central Triplet, and wherein 1, 2, or all 3 nucleotides in said Central Triplet are DNA nucleotides to render the EON more stable and/or more effective in inducing deamination of the target adenosine. In another preferred aspect, the remainder of the EON consists of RNA nucleotides that preferably (but not necessarily) are substituted at the 2' position of the sugar, preferably with 2'-OMe or 2'-MOE modifications. Other ribose modifications that are quite compatible with targeted editing in accordance with the invention are LNA, 2'-F and 2'-NH$_2$. Different combinations of sugar modifications may be applied. In another aspect, the EON according to the invention comprises at least one non-naturally occurring internucleoside linkage modification selected from the group consisting of: phosphorothioate, 3'-methylenephosphonate (i.e. 3'-O-methylphosphonate internucleotide linkage), 5'-methylenephosphonate (i.e. 5'-O-methylphosphonate internucleotide linkage), 3'-phosphoroamidate (i.e. N-3'-phosphoroamidate internucleotide linkage) and 2'-5'- phosphodiester (i.e. 2'-5'-phosphodiester internucleotide linkage). Especially preferred are phosphorothioate linkages.

An EON according to the invention may be indirectly administrated using suitable means known in the art. It may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an EON as identified herein. Accordingly, the invention provides a viral vector expressing an EON according to the invention when placed under conditions conducive to expression of the EON. A cell can be provided with an EON by plasmid-derived EON expression or viral expression provided by adenovirus- or adeno-associated virus-based vectors. Expression may be driven by a polymerase II-promoter (Pol II) such as a U7 promoter or a polymerase III (Pol III) promoter, such as a U6 RNA promoter. A preferred delivery vehicle is AAV, or a retroviral vector such as a lentivirus vector and the like. Also, plasmids, artificial chromosomes, plasmids usable for targeted homologous recombination and integration in the human genome of cells may be suitably applied for delivery of an EON as defined herein. Preferred for the current invention are those vectors wherein transcription is driven from Pol III promoters, and/or wherein transcripts are in the form fusions with U1 or U7 transcripts, which yield good results for delivering small transcripts. It is within the skill of the artisan to design suitable transcripts. Preferred are Pol III driven transcripts, preferably, in the form of a fusion transcript with an U1 or U7 transcript, known to the person skilled in the art.

Typically, when the EON is delivered by a viral vector, it is in the form of an RNA transcript that comprises the sequence of an oligonucleotide according to the invention in a part of the transcript. An AAV vector according to the invention is a recombinant AAV vector and refers to an AAV vector comprising part of an AAV genome comprising an encoded EON according to the invention encapsidated in a protein shell of capsid protein derived from an AAV serotype. Part of an AAV genome may contain the inverted terminal repeats (ITR) derived from an adeno-associated virus serotype, such as AAV1, AAV2, AAV3, AAV4, AAV5, AAV6, AAV7, AAV8, AAV9 and others. Protein shell comprised of capsid protein may be derived from an AAV serotype such as AAV1, 2, 3, 4, 5, 6, 7, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV2 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention. Preferably, a recombinant AAV vector according to the invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector.

More preferably, a recombinant AAV vector according to the invention comprises a capsid protein shell of AAV serotype 2 and the AAV genome or ITRs present in said vector are derived from AAV serotype 5; such vector is referred to as an AAV 2/5 vector. More preferably, a recombinant AAV vector according to the invention comprises a capsid protein shell of AAV serotype 2 and the AAV genome or ITRs present in said vector are derived from AAV serotype 8; such vector is referred to as an AAV 2/8 vector. More preferably, a recombinant AAV vector according to the invention comprises a capsid protein shell of AAV serotype 2 and the AAV genome or ITRs present in said vector are derived from AAV serotype 9; such vector is referred to as an AAV 2/9 vector. More preferably, a recombinant AAV vector according to the invention comprises a capsid protein shell of AAV serotype 2 and the AAV genome or ITRs present in said vector are derived from AAV serotype 2; such vector is referred to as an AAV 2/2 vector. A nucleic acid molecule encoding an EON according to the invention represented by a nucleic acid sequence of choice is preferably inserted between the AAV genome or ITR sequences as identified above, for example an expression construct comprising an expression regulatory element operably linked to a coding sequence and a 3' termination sequence. "AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art. The AAV helper functions can be supplied on an AAV helper construct, which may be a plasmid.

Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand. "AAV helper virus" provides additional functions required for AAV replication and packaging.

Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456. Preferably, an AAV genome as present in a recombinant AAV vector according to the invention does not comprise any nucleotide sequences encoding viral proteins, such as the rep (replication) or cap (capsid) genes of AAV. An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art. A preferred AAV vector according to the invention is an AAV vector, preferably an AAV2/5, AAV2/8, AAV2/9 or AAV2/2 vector, expressing an EON according to the invention that comprises, or preferably consists of, a sequence selected from the group consisting of: SEQ ID NO:1, 2, 3, 4, and 5.

The term 'comprising' encompasses 'including' as well as 'consisting', e.g. a composition comprising X' may consist exclusively of X or may include something additional, e.g. X+Y. The term 'about' in relation to a numerical value x is optional and means, e.g. x±10%. The word 'substantially' does not exclude 'completely', e.g. a composition which is 'substantially free from Y' may be completely free from Y. Where relevant, the word 'substantially' may be omitted from the definition of the invention. The term 'downstream' in relation to a nucleic acid sequence means further along the sequence in the 3' direction; the term 'upstream' means the converse. Thus in any sequence encoding a polypeptide, the start codon is upstream of the stop codon in the sense strand, but is downstream of the stop codon in the antisense strand. References to 'hybridisation' typically refer to specific hybridisation, and exclude non-specific hybridisation. Specific hybridisation can occur under experimental conditions chosen, using techniques well known in the art, to ensure that the majority of stable interactions between probe and target are where the probe and target have at least 70%, preferably at least 80%, more preferably at least 90% sequence identity. The term 'mismatch' is used herein to refer to opposing nucleotides in a double stranded RNA complex which do not form perfect base pairs according to the Watson-Crick base pairing rules. Mismatch base pairs are G-A, C-A, U-C, A-A, G-G, C-C, U-U base pairs. In some aspects EONs of the present invention comprise 0, 1, 2 or 3 mismatches, wherein a single mismatch may comprise several sequential nucleotides. In some aspects EONs of the present invention comprise 0, 1, 2 or 3 wobble base pairs. Wobble base pairs are: G-U, I-U, I-A, and I-C base pairs.

Various chemistries and modifications are known in the field of oligonucleotides that can be readily used in accordance with the invention, see above. The regular internucleosidic linkages between the nucleotides may be altered by mono- or di-thioation of the phosphodiester bonds to yield phosphorothioate esters or phosphorodithioate esters, respectively. Other modifications of the internucleosidic linkages are possible, including amidation and peptide linkers. In a preferred aspect an EON of the present invention has 1, 2, 3, 4 or more phosphorothioate linkages between the most terminal nucleotides of the EON (hence, preferably at both the 5' and 3' end), which means that in the case of 4 phosphorothioate linkages, which is a specifically preferred aspect, the ultimate 5 nucleotides are linked accordingly. It will be understood by the skilled person that the number of such linkages may vary on each end, depending on the target sequence, or based on other aspects, such as toxicity.

In an aspect of the invention, an EON according to the present invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, phosphonoacetate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate. Particularly preferred are internucleoside linkages that are modified to contain a phosphorothioate. Many of these non-naturally occurring modification of the linkage, such as phosphorothioates are chiral, which means that there are Rp and Sp configurations, known to the person skilled in the art. In a preferred aspect, the chirality of the phosphorothioate linkages is controlled, which means that each of the linkages is either in the Rp or in the Sp configuration, whichever is preferred. The choice of an Rp or Sp configuration at a specified linkage position may depend on the target sequence and the efficiency of binding and induction of providing RNA editing. However, if such is not specifically desired, a composition may comprise EONs as active compounds with both Rp and Sp configurations at a certain specified linkage position. Mixtures of such EONs are also feasible, wherein certain positions have preferably either one of the configurations, while for other positions such does not matter.

A further preferred EON comprises one or more sugar moieties that are mono- or di-substituted at the 2', 3' and/or 5' position such as:
—OH;
—F;
substituted or unsubstituted, linear or branched lower (Cl-C10) alkyl, alkenyl, alkynyl, alkaryl, allyl, or aralkyl, that may be interrupted by one or more heteroatoms;
—O-, S-, or N-alkyl (e.g. —O-methyl);
—O-, S-, or N-alkenyl;
—O-, S-, or N-alkynyl;
—O-, S-, or N-allyl;
—O-alkyl-O-alkyl;
-methoxy;
-aminopropoxy;
-methoxyethoxy;
-dimethylamino oxyethoxy; and
-dimethylaminoethoxyethoxy.

The sugar moiety can be a pyranose or derivative thereof, or a deoxypyranose or derivative thereof, preferably ribose or derivative thereof, or deoxyribose or derivative thereof. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid. These substitutions render the nucleotide analogue or equivalent RNase H and nuclease resistant and increase the affinity for the target RNA.

In another aspect, a nucleotide analogue or equivalent within the EON comprises one or more base modifications or substitutions. Modified bases comprise synthetic and natural bases such as inosine, xanthine, hypoxanthine and other-aza, deaza, -hydroxy, -halo, -thio, thiol, -alkyl, -alkenyl, -alkynyl, thioalkyl derivatives of pyrimidine and purine bases that are or will be known in the art. Purine nucleobases and/or pyrimidine nucleobases may be modified to alter their properties, for example by amination or deamination of the heterocyclic rings. The exact chemistries and formats may depend from oligonucleotide construct to oligonucleotide construct and from application to application, and may be worked out in accordance with the wishes and preferences of those of skill in the art. It is believed in the art that 4 or more consecutive DNA nucleotides in an oligonucleotide create so-called 'gapmers' that—when annealed to their RNA cognate sequences—induce cleavage of the target RNA by RNase H. According to the present invention, RNase H cleavage of the target RNA is generally to be avoided as much as possible.

An EON according to the invention is normally longer than 10 nucleotides, preferably more than 11, 12, 13, 14, 15, 16, still more preferably more than 17 nucleotides. In one aspect the EON according to the invention is longer than 20 nucleotides. The oligonucleotide according to the invention is preferably shorter than 100 nucleotides, still more preferably shorter than 60 nucleotides, still more preferably shorter than 50 nucleotides. In a preferred aspect, the oligonucleotide according to the invention comprises 18 to 70 nucleotides, more preferably comprises 18 to 60 nucleotides, and even more preferably comprises 18 to 50 nucleotides. Hence, in a particularly preferred aspect, the oligonucleotide of the present invention comprises 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. In another preferred aspect, at either end or both of the termini of an EON according to the present invention inverted deoxyT or dideoxyT nucleotides may be incorporated.

It is known in the art, that RNA editing entities (such as human ADAR enzymes) edit dsRNA structures with varying specificity, depending on a number of factors. One important factor is the degree of complementarity of the two strands making up the dsRNA sequence. Perfect complementarity of the two strands usually causes the catalytic domain of hADAR to deaminate adenosines in a non-discriminative manner, reacting more or less with any adenosine it encounters. The specificity of hADAR1 and 2 can be increased by ensuring a number of mismatches in the dsRNA, which presumably help to position the dsRNA binding domains in a way that has not been clearly defined yet. Additionally, the deamination reaction itself can be enhanced by providing an EON that comprises a mismatch opposite the adenosine to be edited. The mismatch is preferably created by providing a targeting portion having a cytidine opposite the adenosine to be edited. As an alternative, also uridines may be used opposite the adenosine, which, understandably, will not result in a 'mismatch' because U and A pair. Upon deamination of the adenosine in the target strand, the target strand will obtain an inosine which, for most biochemical processes, is "read" by the cell's biochemical machinery as a G. Hence, after A to I conversion, the mismatch has been resolved, because I is perfectly capable of base pairing with the opposite C in the targeting portion of the oligonucleotide construct according to the invention. After the mismatch has been resolved due to editing, the substrate is released and the oligonucleotide construct-editing entity complex is released from the target RNA sequence, which then becomes available for downstream biochemical processes, such as splicing and translation. The desired level of specificity of editing the target RNA sequence may depend from application to application. Following the instructions in the present disclosure, those of skill in the art will be capable of designing the complementary portion of the oligonucleotide according to their needs, and, with some trial and error, obtain the desired result.

The teaching of the present invention can also be used to edit target RNA sequences in cells within a so-called organoid, such as in vitro generated eye cups. The treated cells, in the organoid, or in vivo, or in vitro or in ex vivo situations will generally have a genetic mutation in which an adenosine is targeted. The mutation may be heterozygous or homozygous. The invention will typically be used to modify point mutations, such as N to A mutations, wherein N may be G, C, U (on the DNA level T), preferably G to A mutations, or N to C mutations, wherein N may be A, G, U (on the DNA level T), preferably U to C mutations. Table 1 displays a range of pathogenic G>A mutations found in the USH2A gene (and reported in literature), all of which may potentially be targeted by an EON according to the present invention. It is noted that not all (potentially possible) mutations are given here, because an EON of the present invention may also be applied to target an adenosine that is not the result of a G>A mutation, but that is part of a premature stop codon, due to the mutation in fact being the appearance of a T or G. For instance, when a wild type TCA codon (serine) is mutated to TGA (stop) due to a C>G mutation, then targeting the A using an EON according to the present invention changes that stop codon to TGG (tryptophan) that may be tolerated in the usherin protein. Another example may be a wild type AAA codon (lysine) that is mutated to TAA (stop) due to an A>T mutation, then targeting the 5' A using an EON according to the present invention changes that stop codon to GAA (glutamate) that may be tolerated in the usherin protein.

TABLE 1

Pathogenic mutations in exons and introns of the human USH2A gene. Most of the given mutations in exons lead to premature termination of protein translation.

| Mutation | Location | Protein |
|---|---|---|
| c.633G > A | Exon 3 | p.(Trp211*) |
| c.956G > A | Exon 6 | p.(Cys319Tyr) |
| c.1227G > A | Exon 7 | p.(Trp409*) |
| c.3251G > A | Exon 16 | p.(Trp1084*) |
| c.3788G > A | Exon 17 | p.(Trp1263*) |
| c.4821G > A | Exon 23 | p.(Trp1607*) |
| c.5399G > A | Exon 27 | p.(Trp1800*) |
| c.5522G > A | Exon 27 | p.(Gly1841Glu) |
| c.6488G > A | Exon 34 | p.(Trp2163*) |
| c.7854G > A | Exon 41 | p.(Trp2618*) |
| c.7931G > A | Exon 41 | p.(Trp2644*) |
| c.8141G > A | Exon 41 | p.(Trp2714*) |
| c.8231G > A | Exon 42 | p.(Trp2744*) |
| c.8232G > A | Exon 42 | p.(Trp2744*) |
| c.8522G > A | Exon 42 | p.(Trp2841*) |
| c.8628G > A | Exon 43 | p.(Trp2876*) |
| c.8834G > A | Exon 44 | p.(Trp2945*) |
| c.8835G > A | Exon 44 | p.(Trp2945*) |
| c.8981G > A | Exon 45 | p.(Trp2994*) |
| c.9120G > A | Exon 46 | p.(Trp3040*) |
| c.9449G > A | Exon 48 | p.(Trp3150*) |
| c.9450G > A | Exon 48 | p.(Trp3150*) |
| c.11105G > A | Exon 57 | p.(Trp3702*) |
| c.11754G > A | Exon 61 | p.(Trp3918*) |
| c.11864G > A | Exon 61 | p.(Trp3955*) |
| c.12729G > A | Exon 63 | p.(Trp4243*) |
| c.13313G > A | Exon 63 | p.(Trp4438*) |
| c.14139G > A | Exon 65 | p.(Trp4713*) |
| c.14175G > A | Exon 65 | p.(Trp4725*) |
| c.14180G > A | Exon 65 | p.(Trp4727*) |
| c.651+1G > A | Intron 03i | p.(?) |
| c.1644+1G > A | Intron 09i | p.(?) |
| c.1840+1G > A | Intron 10i | p.(?) |
| c.2167+5G > A | Intron 12i | p.[Ile658Glyfs*33, Gln714_Gly723del] |
| c.2809+1G > A | Intron 13i | p.(?) |
| c.3157+35G > A | Intron 15i | p.(?) |

TABLE 1-continued

Pathogenic mutations in exons and introns of the human USH2A gene. Most of the given mutations in exons lead to premature termination of protein translation.

| Mutation | Location | Protein |
|---|---|---|
| c.3317−1G > A | Intron 16i | p.(?) |
| c.4758+1G > A | Intron 22i | p.(?) |
| c.5776+1G > A | Intron 28i | p.(?) |
| c.5858−1G > A | Intron 29i | p.(?) |
| c.6325+1G > A | Intron 32i | p.(?) |
| c.7301−1G > A | Intron 38i | p.(?) |
| c.7452−1G > A | Intron 39i | p.(?) |
| c.8223+1G > A | Intron 41i | p.(?) |
| c.9258+1G > A | Intron 46i | p.(?) |
| c.9570+1G > A | Intron 48i | p.(?) |
| c.11047+1G > A | Intron 56i | p.(?) |
| c.11549−1G > A | Intron 59i | p.(?) |
| c.14133+1G > A | Intron 64i | p.(?) |
| c.15053−1G > A | Intron 69i | p.(?) |

Preferably premature stop codons are targeted, such that translation can continue after editing. More preferably, the RNA editing results in a wild type protein. Those of ordinary skill in the art will understand that the applicability of the current invention is very wide, but most preferably, an EON of the present invention is used for the treatment of Usher syndrome, caused by a genetic defect in the USH2A gene. Preferably, premature stop codons in mutated USH2A pre-mRNA and mRNA are edited to allow continued translation. In the non-limiting examples below, the inventors targeted the adenosine of the c.11864G>A mutation in exon 61 (see Table 1) and showed that it is possible to deaminate this adenosine very specifically using an EON according to the present invention. It is held that the applicability taught by the present disclosure is not limited to USH2A exon 61, or this particular mutation, but that any USH2A mutation where exon skipping is not a feasible option and in which A>I deamination by RNA editing would be beneficial, can potentially be targeted using the teaching brought forward by the inventors herein.

The invention also relates to a pharmaceutical composition comprising an EON of the invention and a pharmaceutically acceptable carrier. In some aspects of the invention the pharmaceutically acceptable carrier can simply be a saline solution. This can usefully be isotonic or hypotonic, particularly for pulmonary delivery. The invention also provides a delivery device (e.g. syringe) which includes a pharmaceutical composition of the invention. The oligonucleotide according to the invention is suitably administrated in aqueous solution, e.g. saline, or in suspension, optionally comprising additives, excipients and other ingredients, compatible with pharmaceutical use, at concentrations ranging from 1 ng/ml to 1 g/ml, preferably from 10 ng/ml to 500 mg/ml, more preferably from 100 ng/ml to 100 mg/ml. Dosage may suitably range from between about 1 µg/kg to about 100 mg/kg, preferably from about 10 µg/kg to about 10 mg/kg, more preferably from about 100 µg/kg to about 1 mg/kg. Administration may be by direct injection in the vitreous in the eye. Administration may be in any form compatible with pharmaceutical use in humans.

The invention also relates to an EON of the invention for use in a method for making a change in a target RNA sequence in a mammalian, preferably human cell, as described herein, preferably for use in the treatment of Usher syndrome. Similarly, the invention provides the use of an EON of the invention in the manufacture of a medicament for making a change in a target RNA sequence in a mammalian, preferably human cell, as described herein, preferably for the treatment of Usher syndrome.

The invention also relates to a method for the deamination of at least one specific target adenosine present in a target RNA molecule in a cell, wherein said target RNA molecule is an USH2A pre-mRNA molecule or an USH2A mRNA molecule, said method comprising the steps of: providing said cell with an EON according to the invention; allowing uptake by the cell of said EON; allowing annealing of said EON to the target RNA molecule; allowing a mammalian ADAR enzyme comprising a natural dsRNA binding domain as found in the wild type enzyme to deaminate said target adenosine in said target RNA molecule to an inosine; and optionally identifying the presence of said inosine in the RNA molecule. Introduction of the EON according to the present invention into the cell is performed by general methods known to the person skilled in the art. After deamination the read-out of the effect (alteration of the target RNA sequence) can be monitored through different ways. Hence, the identification step of whether the desired deamination of the target adenosine has indeed taken place depends generally on the position of the target adenosine in the target RNA sequence, and the effect that is incurred by the presence of the adenosine (point mutation, early stop codon, aberrant splice site, alternative splice site, misfolding of the resulting protein, etc.). Hence, in a preferred aspect, depending on the ultimate deamination effect of A-to-I conversion, the identification step comprises: sequencing the target RNA sequence; assessing the presence of a functional, elongated, full length and/or wild type protein when said target adenosine is located in a UGA or UAG stop codon, which is edited to a UGG codon through said deamination; assessing the presence of a functional, elongated, full length and/or wild-type protein when two target adenosines are located in a UAA stop codon, which is edited to a UGG codon through the deamination of both target adenosines; assessing whether splicing of the pre-mRNA was altered by said deamination; and/or using a functional read-out, wherein the target RNA after said deamination encodes a functional, full length, elongated and/or wild type protein. In the event that there is a UAA stop codon it means that both adenosines need to be deaminated. Hence, the invention also relates to oligonucleotides and methods wherein two adenosines that are next to each other are co-deaminated by an RNA editing enzyme such as ADAR. In this particular case, the UAA stop codon is converted into a UGG Trp-encoding codon. Because the deamination of the adenosine to an inosine may result in a protein that is no longer suffering from the mutated A at the target position, the identification of the deamination into inosine may also be a functional read-out, for instance an assessment on whether a functional protein is present, or even the assessment that a disease that is caused by the presence of the adenosine is (partly) reversed. The functional assessment for usherin will generally be according to methods known to the skilled person. When the presence of a target adenosine causes aberrant splicing, the read-out may be the assessment of whether the aberrant splicing is still taking place, or not, or less. On the other hand, when the deamination of a target adenosine is wanted to introduce a splice site, then similar approaches can be used to check whether the required type of splicing is indeed taking place. A very suitable manner to identify the presence of an inosine after deamination of the target adenosine are RT-PCR and sequencing, using methods that are well-known to the person skilled in the art.

The invention relates to an RNA editing oligonucleotide (EON) capable of forming a double stranded complex with a target RNA molecule, wherein the EON when complexed with the target RNA molecule, and further complexed with an Adenosine Deaminase acting on RNA (ADAR), is capable of deaminating a target adenosine in the target RNA molecule, wherein the EON comprises a Central Triplet of three sequential nucleotides, wherein the nucleotide directly opposite the target adenosine is the middle nucleotide of the Central Triplet, and wherein the target RNA molecule is a human USH2A pre-mRNA or mRNA, or a part thereof. Preferably, the middle nucleotide of the Central Triplet is a cytidine. In another preferred aspect, one, two or three nucleotides in the Central Triplet comprise a modification, with the proviso that the middle nucleotide does not have a 2'-OMe modification in the sugar moiety. In another preferred aspect, the modification is selected from the group consisting of deoxyribose (DNA), Unlocked Nucleic Acid (UNA) and 2'-fluororibose. The invention also relates to an EON according to the invention, wherein the EON comprises at least one non-naturally occurring internucleoside linkage modification selected from the group consisting of phosphorothioate, 3'-methylenephosphonate, 5'-methylenephosphonate, 3'-phosphoroamidate and 2'-5'-phosphodiester. Preferably, the two, three, four, five, or six terminal nucleotides of the 5' and 3' terminus of the EON are linked with phosphorothioate linkages, preferably wherein the terminal five nucleotides at the 5' and 3' terminus are linked with phosphorothioate linkages. In one particular preferred aspect, the invention relates to an EON according to the invention, wherein one or more nucleotides in the EON outside the Central Triplet comprise a mono- or disubstitution at the 2', 3' and/or 5' position of the sugar, selected from the group consisting of: —OH; —F; substituted or unsubstituted, linear or branched lower (CI-C10) alkyl, alkenyl, alkynyl, alkaryl, allyl, or aralkyl, that may be interrupted by one or more heteroatoms; —O-, S-, or N-alkyl (e.g. —O-methyl); —O-, S-, or N-alkenyl; —O-, S-, or N-alkynyl; —O-, S-, or N-allyl; —O-alkyl-O-alkyl; -methoxy; -aminopropoxy; -methoxyethoxy; -dimethylamino oxyethoxy; and -dimethylaminoethoxyethoxy. In a more preferred aspect the target adenosine targeted by the EON according to the invention, is part of a premature stop codon in the human USH2A pre-mRNA or mRNA, and even more preferably wherein the premature stop codon is caused by the c.11864G>A mutation in exon 61 of the USH2A gene. Even more preferred are EON according to the invention, wherein the EON comprises or consists of the sequence selected from the group consisting of: SEQ ID NO:1, 2, 3, 4, and 5.

The invention also relates to a pharmaceutical composition comprising an EON according to the invention, and a pharmaceutically acceptable carrier. The invention also relates to an EON according to the invention for use in the treatment of Usher syndrome. In yet another aspect, the invention relates to a use of an EON according to the invention in the manufacture of a medicament for the treatment of Usher syndrome.

The invention, in yet another aspect, relates to a method for the deamination of at least one specific target adenosine present in a target RNA molecule in a cell, wherein the target RNA molecule is a human USH2A pre-mRNA or mRNA, or a part thereof, the method comprising the steps of: providing the cell with an EON according to the invention; allowing uptake by the cell of the EON; allowing annealing of the EON to the target RNA molecule; allowing a mammalian ADAR enzyme comprising a natural dsRNA binding domain as found in the wild type enzyme to deaminate the target adenosine in the target RNA molecule to an inosine; and optionally identifying the presence of the inosine in the target RNA molecule. Preferably, said cell is a human cell, more preferably a cell in vivo, or ex vivo from an Usher patient, preferably an Usher patient carrying a mutated USH2A gene, more preferably wherein the USH2A gene is mutated by the presence of a premature stop codon in the USH2A transcript, most preferably wherein the premature stop codon is caused by the c.11864A>G mutation. In a preferred aspect, the step of identifying the inosine after deamination comprises: sequencing the target RNA molecule; assessing the presence of a functional, elongated, full length and/or wild type usherin protein when the target adenosine is located in a UGA or UAG stop codon, which is edited to a UGG codon through the deamination; assessing whether splicing of the pre-mRNA was altered by the deamination; or using a functional read-out, wherein the target RNA after the deamination encodes a functional, full length, elongated and/or wild type usherin protein. In yet another aspect the invention relates to a method of treating a patient with Usher syndrome, comprising the steps of formulating an EON according to the invention into a pharmaceutical formulation suitable for administration in the eye; and administering said formulation into the vitreous of one or both eyes of said patient to allow deamination of the target adenosine in the USH2A pre-mRNA or USH2A mRNA to take place in the photoreceptor cells in the eye. Preferably, the method of treatment according to the invention is for the treatment of a patient carrying a c.11864G>A mutation in exon 61 of the USH2A gene.

SEQUENCES
(EON hUsh2a-1, the 3' T is an inverted deoxyT)
                                           SEQ ID NO: 1
GAGCUUCCAGAGUUUGUGUUAAUGGCCACAGACUCUCCT (EON hUsh2a-2, the 3' T is an inverted deoxyT, the 5' T is an inverted dideoxyT)
                                           SEQ ID NO: 2
TGAGCUUCCAGAGUUUGUGUUAAUGGCCACAGACUCUCCT (EON hUsh2a-3)
                                           SEQ ID NO: 3
GAGCUUCCAGAGUUUGUGUUAAUGGCCAUAGAUUCUUC (EON hUsh2a-4)
                                           SEQ ID NO: 4
GAGCUUCCAGCGUUGGUGUUAAUGGCCACAGACUCUCC (EON hUsh2a-5)
                                           SEQ ID NO: 5
GAGCUUCCAGAGUUUGUGGUAAUGGCCACAGACUCUCC (G-block comprising mutated exon 61 of human USH2A; mutation underlined)
                                           SEQ ID NO: 6
GGCTAGAGTACT*TAATACGACTCACTATAGG*CTAGCCTCGAGAATTCcgg aggtcaacaacgagtcttttgtcatctacatgttcgtggtccacttcacc atcccatgattatcatctttttctgctatgggcagctcgtcttcaccgt caaggagACGCCCTGCTGGCATTGAAGAGGAGTCTGTTTTATTTGTCTGG

TCAGAAGGAGCCCTTGAATTTATGGATGAAGGAGACACCCTGAGGCCTTT

CACACTCTACGAATATCGGGTCAGAGCCTGTAACTCCAAGGGTTCAGTGG

AGAGTCTGTAGTCATTAACACAAACTCTGGAAGCTCCACCTCAAGATTTT

CCAGCTCCTTGGGCTCAAGCCACGAGTGCTCATTCAGTTCTGTTGAATTG

GACAAAGCCAGAATCTCCCAATGGCATTATCTCCCATTACCGTGTGGTCT

ACCAGGAGAGACCCGACGATCCTACATTTAACAGCCCTACCGTGCATGCT

-continued

TTCACAGTGAAGttccggaactgc*atgctcaccaccatctgct*gcggcaa gaacccactgggtgacgatgaggcctctgctaccgtgtccaagacggaga cgagccaggtggcccoggcctaagacctgcctaggactctgtggccgact ataggcgtctcccatccctacacctgtcgac*CCGGGCGGCCGCTTCCCT*

*T*

(human exon 61, mutated, c.11864G > A mutation underlined)

SEQ ID NO: 7

ACGCCCTGCTGGCATTGAAGAGGAGTCTGTTTTATTTGTCTGGTCAGAAG

GAGCCCTTGAATTTATGGATGAAGGAGACACCCTGAGGCCTTTCACACTC

TACGAATATCGGGTCAGAGCCTGTAACTCCAAGGGTTCAGTGGAGAGTCT

GT<u>A</u>GTCATTAACACAAACTCTGGAAGCTCCACCTCAAGATTTTCCAGCTC

CTTGGGCTCAAGCCACGAGTGCTCATTCAGTTCTGTTGAATTGGACAAAG

CCAGAATCTCCCAATGGCATTATCTCCCATTACCGTGTGGTCTACCAGGA

GAGACCCGACGATCCTACATTTAACAGCCCTACCGTGCATGCTTTCACAG

TGAAG (forward PCR primer)

SEQ ID NO: 8

TAATACGACTCACTATAGG (reverse PCR primer)

SEQ ID NO: 9

GCAGATGGTGGTGAGCAT (part of the mutated exon 61 sequence; RNA; FIG. 3; the mutation is underlined)

SEQ ID NO: 10

GGGUUCAGUGGAGAGUCUGU<u>A</u>GUCAUUAACACAAACUCUGGAAGCUCCAC

CUCAAGAUUUUCCA (PCR primer forward)

SEQ ID NO: 11

TACATGTTCGTGGTCCACTTC (PCR primer reverse)

SEQ ID NO: 12

GCAGATGGTGGTGAGCAT (target sequence in FIG. 4)

SEQ ID NO: 13

CTGTAGTCA

EXAMPLES

Example 1. RNA Editing of the c.11864G>A Mutation in Exon 61 of the Human USH2A Gene The inventors of the present invention realized that, although great progress was being made in the art using antisense oligonucleotides to skip aberrant and/or mutated exons from human USH2A pre-mRNA to treat Usher syndrome, no such therapy would be available for Usher patients carrying pathogenic mutations in exons that are not in-frame with their neighbouring exons and that could not be skipped. Moreover, also patients that would suffer from Usher syndrome due to mutations in -in-frame exons, but wherein exon skipping would render the usherin protein non-functional would also not benefit from exon-skipping therapies. They questioned whether it would be possible to use a different RNA targeting technology to specifically target such mutations in the pre-mRNA or mRNA of the mutated USH2A transcript, without the need of exon skipping. One such technology is the recently developed RNA editing technology.

As a non-limiting example the inventors of the present invention selected the c.11864G>A mutation in exon 61, which is a pathogenic, and Usher syndrome-causing mutation. Exon 61 (355 bp) cannot be skipped as it is not in-frame with its neighbouring exons. Hence, skipping exon 61 is not a therapeutic option. The c.11864G>A mutation results in a premature termination codon in which a UGG codon (for tryptophan) is mutated to UAG (stop). The mutation on a protein level is referred to as p.(Trp3955*), see Table 1, and was described in 2004 (Van Wijk, E. et al. 2004. Identification of 51 novel exons of the Usher syndrome type 2A (USH2A) gene that encode multiple conserved functional domains and that are mutated in patients with Usher syndrome type II. Am J Hum Genet 74:738-744). Deamination of the adenosine to an inosine results in reversal to a wild protein with a tryptophan encoding codon (UGG>UAG>UIG>UGG).

The 355 bp sequence of exon 61 (SEQ ID NO:7) is shown in FIG. 2, from 5' to 3'. The c.11864G>A mutation is underlined. To obtain RNA of exon 61, first a PCR was performed using an USH2A G-block (IDT) as a template (FIG. 1; SEQ ID NO:6), which contained the sequence for the T7 promotor and the RHO exon 3 sequence (upstream), the sequence of USH2A exon 61, and the RHO exon 5 sequence, and using forward primer 5'-TAATACGACT-CACTATAGG-3' (SEQ ID NO:8) and reverse primer 5'-GCAGATGGTGGTGAGCAT-3' (SEQ ID NO:9) using general methods known to the person skilled in the art. The PCR product was then used as template for in vitro transcription, applying the MEGAscript T7 transcription kit. The resulting RNA was purified on a urea gel and then extracted in 50 mM Tris-Cl pH 7.4, 10 mM EDTA, 0.1% SDS, 0.3 M NaCl buffer and phenol-chloroform purified. This purified RNA was used as target in the biochemical editing assay.

Initially, five RNA editing oligonucleotides were designed and generated: hUsh2a-1, hUsh2a-2, hUsh2a-3, hUsh2a-4, and hUsh2a-5 (SEQ ID NO:1, 2, 3, 4, and 5, respectively).

Example 2. RNA Editing of the Adenosine in the c.11864G>A Mutation in Exon 61 of Human USH2A Using a Biochemical Assay The mutated exon 61 RNA was used in a biochemical assay in which it was determined whether one or more of the five initially designed RNA editing oligonucleotides (hUsh2a-1 to 5) were capable of specifically deaminating the adenosine of the c.11864G>A mutation. FIG. 3 shows the target RNA (partly; SEQ ID NO:10) and the five EONs in 3' to 5' that are complementary to the target sequence (except for the wobble base pairs and mismatches, as indicated). Specifics are given in the legend.

First, the five EONs were annealed to the target RNA. Annealing was done in a buffer (5 mM Tris-Cl pH 7.4, 0.5 mM EDTA and 10 mM NaCl) at the ratio 1:3 of target RNA to EON (6 nM EON and 2 nM target). A sample with RNA but lacking an EON, was taken as a negative control. The samples were heated at 95° C. for 3 min and then slowly cooled down to RT. Next, the editing reaction was carried out. The annealed EON and target RNA was mixed with protease inhibitor (cOmplete™, Mini, EDTA-free Protease I, Sigma-Aldrich), RNase inhibitor (RNasin, Promega), poly A (Qiagen), tRNA (Invitrogen) and editing reaction buffer (15 mM Tris-Cl pH 7.4, 1.5 mM EDTA, 3% glycerol, 60 mM KCl, 0.003% NP-40, 3 mM MgCl$_2$ and 0.5 mM DTT). The reaction was started by adding purified ADAR2, which was produced by GenScript, to a final concentration of 8 nM into the mix and incubated for 1 h at 37° C. The reaction was stopped by adding 190 uL boiling water and then the mixture was incubated for 5 min at 95° C. The stopped reaction mixture was then used as template for cDNA synthesis using Maxima reverse transcriptase and hexamer (Thermo Fisher). The cDNA was diluted 10× and 2 µL of this dilution was used as template for PCR. The PCR reaction was performed with the following primers: forward primer 5'-TACATGTTCGTGGTCCACTTC-3' and reverse primer 5'-GCAGATGGTGGTGAGCAT-3'. The PCR product was then sequenced (BaseClear) using the same primers. The results of this sequencing are shown in FIG. 4. Editing was clearly observed by a shift in peak intensity from A to G in the sequencing chromatogram, in each of the samples in which an EON was added, both observed with the forward as the reverse sequencing. The ratio of the heights of the A and G peaks was used to determine the A-to-I editing percentage. No editing was observed in the samples in which no EON was added.

These results convincingly show that the inventors were able to obtain on target RNA editing of an adenosine in a target RNA molecule, wherein the target RNA molecule represented a mutated (pre-) mRNA from a mutated gene causing an ocular disease, paving the way towards potential clinical treatments of genetic eye diseases using EONs and thereby employing endogenous RNA deaminases. A next step is to obtain an increase in specificity, using the teaching as disclosed herein, and making use of a variety of chemical modifications, lengths, wobble base pairs and mismatches, and/or combinations thereof. Experiments are performed using overexpression systems in cells, and eye cups produced from patients carrying the c.11864G>A mutation, for determining the in vivo effect of the EON according to the present invention. The editing of an adenosine using the c.11864G>A mutation in exon 61 of human USH2A, known to cause Usher syndrome in human patients, as disclosed herein only serves as a non-limiting example of all genetic eye diseases caused by mutations in which an A to G reversal (via inosine) would be beneficial and for which other RNA targeting technologies, such as exon skipping, are not suitable. However, the treatment of Usher syndrome is preferred.

The invention claimed is:

1. An RNA editing oligonucleotide (EON) comprising a sequence selected from the group consisting of: SEQ ID NO:1, 2, 3, 4, and 5.

2. The EON according to claim 1, wherein the EON does not comprise a recruitment portion.

3. The EON according to claim 1, wherein one, two or three nucleotides in the Central Triplet of the EON comprise a modification, with the proviso that the middle nucleotide does not have a 2'-OMe modification in the sugar moiety.

4. The EON according to claim 3, wherein the modification is selected from the group consisting of deoxyribonucleosides (DNA), Unlocked Nucleic Acid (UNA) and 2'-fluororibose.

5. The EON according to claim 1, wherein the EON comprises at least one non-naturally occurring internucleoside linkage modification selected from the group consisting of phosphorothioate, 3'-methylenephosphonate, 5'-methylenephosphonate, 3'-phosphoroamidate and 2'-5'-phosphodiester.

6. The EON according to claim 5, wherein the two, three, four, five, or six terminal nucleotides of the 5' and 3' terminus of the EON are linked with phosphorothioate linkages.

7. The EON according to claim 1, wherein one or more nucleotides outside the Central Triplet of the EON comprise a mono- or disubstitution at the 2', 3' and/or 5' position of the sugar, selected from the group consisting of: —OH; —F; substituted or unsubstituted, linear or branched lower (C1-C10) alkyl, alkenyl, alkynyl, alkaryl, allyl, or aralkyl, that may be interrupted by one or more heteroatoms; —O-, S-, or N-alkyl; —O-, S-, or N-alkenyl; —O-, S-, or N-alkynyl; —O-, S-, or N-allyl; —O-alkyl-O-alkyl; -methoxy; -aminopropoxy; -methoxyethoxy; -dimethylamino oxyethoxy; and -dimethylaminoethoxyethoxy.

8. The RNA editing oligonucleotide of claim 1 consisting of the sequence selected from the group consisting of: SEQ ID NO:1, 2, 3, 4, and 5.

9. A pharmaceutical composition comprising an EON according to claim 1, and a pharmaceutically acceptable carrier.

10. An oligonucleotide comprising the sequence SEQ ID NO: 5 and comprising at least one non-naturally occurring internucleoside linkage modification selected from the group consisting of phosphorothioate, 3'-methylenephosphonate, 5'-methylenephosphonate, 3'-phosphoroamidate and 2'-5'-phosphodiester.

11. The oligonucleotide according to claim 10, wherein the two, three, four, five, or six terminal nucleotides of the 5' and 3' terminus of the oligonucleotide are linked with phosphorothioate linkages.

12. The oligonucleotide according to claim 10, wherein one or more nucleotides comprise a mono- or di-substitution at the 2', 3' and/or 5' position of the sugar, selected from the group consisting of: —OH; —F; substituted or unsubstituted, linear or branched lower (C1-C10) alkyl, alkenyl, alkynyl, alkaryl, allyl, or aralkyl, that may be interrupted by one or more heteroatoms; —O-, S-, or N-alkyl; —O-, S-, or N-alkenyl; —O-, S-, or N-alkynyl; —O-, S-, or N-allyl; —O-alkyl-O-alkyl; -methoxy; -aminopropoxy; -methoxyethoxy; -dimethylamino oxyethoxy; and -dimethylaminoethoxyethoxy.

13. The oligonucleotide of claim 10, wherein one or more nucleotides is an RNA monomer.

14. The oligonucleotide of claim 13, wherein at least one of the RNA monomers is a 2'-O-methyl RNA monomer or a 2'-O-(2-methoxyethyl) RNA monomer.

15. The oligonucleotide of claim 14, comprising the nucleotide sequence of gagcuuccag aguuuguggu aauggcCAca gacucucc (SEQ ID NO: 5) wherein all of the nucleotides are 2'-O-methyl RNA monomers except for the nucleotides in uppercase, which are DNA monomers.

* * * * *

SEQUENCE LISTING

```
<160> NUMBER OF SEQ ID NOS: 12

<210> SEQ ID NO 1
<211> LENGTH: 39
<212> TYPE: DNA
<213> ORGANISM: Artificial sequence
<220> FEATURE:
<223> OTHER INFORMATION: EON hUsh2a-1
<220> FEATURE:
<221> NAME/KEY: misc_feature
<222> LOCATION: (39)..(39)
<223> OTHER INFORMATION: inverted deoxyT

<400> SEQUENCE: 1
gagcuuccag aguuuguguu aauggccaca gacucucct                39

<210> SEQ ID NO 2
<211> LENGTH: 40
<212> TYPE: DNA
<213> ORGANISM: Artificial sequence
<220> FEATURE:
<223> OTHER INFORMATION: EON hUsh2a-2
<220> FEATURE:
<221> NAME/KEY: misc_feature
<222> LOCATION: (1)..(1)
<223> OTHER INFORMATION: inverted dideoxyT
<220> FEATURE:
<221> NAME/KEY: misc_feature
<222> LOCATION: (40)..(40)
<223> OTHER INFORMATION: inverted deoxyT

<400> SEQUENCE: 2
tgagcuucca gaguuugugu uaauggccac agacucucct               40

<210> SEQ ID NO 3
<211> LENGTH: 38
<212> TYPE: DNA
<213> ORGANISM: Artificial sequence
<220> FEATURE:
<223> OTHER INFORMATION: EON hUsh2a-3

<400> SEQUENCE: 3
gagcuuccag aguuuguguu aauggccaua gauucuuc                 38
```

<210> SEQ ID NO 4
<211> LENGTH: 38
<212> TYPE: DNA
<213> ORGANISM: Artificial sequence
<220> FEATURE:
<223> OTHER INFORMATION: EON hUsh2a-4

<400> SEQUENCE: 4
gagcuuccag cguugguguu aauggccaca gacucucc                           38

<210> SEQ ID NO 5
<211> LENGTH: 38
<212> TYPE: DNA
<213> ORGANISM: Artificial sequence
<220> FEATURE:
<223> OTHER INFORMATION: EON hUsh2a-5

<400> SEQUENCE: 5
gagcuuccag aguuuguggu aauggccaca gacucucc                           38

<210> SEQ ID NO 6
<211> LENGTH: 701
<212> TYPE: DNA
<213> ORGANISM: Artificial sequence
<220> FEATURE:
<223> OTHER INFORMATION: G-block comprising mutated exon 61 of human
    USH2A

<400> SEQUENCE: 6
ggctagagta cttaatacga ctcactatag gctagcctcg agaattccgg aggtcaacaa    60
cgagtctttt gtcatctaca tgttcgtggt ccacttcacc atccccatga ttatcatctt   120
tttctgctat gggcagctcg tcttcaccgt caaggagacg ccctgctggc attgaagagg   180
agtctgtttt atttgtctgg tcagaaggag cccttgaatt tatggatgaa ggagacaccc   240
tgaggccttt cacactctac gaatatcggg tcagagcctg taactccaag ggttcagtgg   300
agagtctgta gtcattaaca caaactctgg aagctccacc tcaagatttt ccagctcctt   360
gggctcaagc cacgagtgct cattcagttc tgttgaattg acaaagcca gaatctccca    420 atggcattat ctcccattac cgtgtggtct accaggagag acccgacgat cctacattta   480
acagccctac cgtgcatgct ttcacagtga agttccggaa ctgcatgctc accaccatct   540
gctgcggcaa gaacccactg ggtgacgatg aggcctctgc taccgtgtcc aagacggaga   600
cgagccaggt ggccccggcc taagacctgc ctaggactct gtggccgact ataggcgtct   660
cccatcccct acacctgtcg acccgggcgg ccgcttccct t                      701

<210> SEQ ID NO 7
<211> LENGTH: 355
<212> TYPE: DNA
<213> ORGANISM: Homo sapiens

<400> SEQUENCE: 7
acgccctgct ggcattgaag aggagtctgt tttatttgtc tggtcagaag gagcccttga    60
atttatggat gaaggagaca ccctgaggcc tttcacactc tacgaatatc gggtcagagc   120
ctgtaactcc aagggttcag tggagagtct gtagtcatta acacaaactc tggaagctcc   180
acctcaagat tttccagctc cttgggctca gccacgagt gctcattcag ttctgttgaa    240
ttggacaaag ccagaatctc ccaatggcat tatctcccat taccgtgtgg tctaccagga   300
gagacccgac gatcctacat ttaacagccc taccgtgcat gctttcacag tgaag       355

```
<210> SEQ ID NO 8
<211> LENGTH: 19
<212> TYPE: DNA
<213> ORGANISM: Artificial sequence
<220> FEATURE:
<223> OTHER INFORMATION: forward PCR primer

<400> SEQUENCE: 8
taatacgact cactatagg                                                    19

<210> SEQ ID NO 9
<211> LENGTH: 18
<212> TYPE: DNA
<213> ORGANISM: Artificial sequence
<220> FEATURE:
<223> OTHER INFORMATION: reverse PCR primer

<400> SEQUENCE: 9
gcagatggtg gtgagcat                                                     18

<210> SEQ ID NO 10
<211> LENGTH: 64
<212> TYPE: RNA
<213> ORGANISM: Homo sapiens

<400> SEQUENCE: 10
ggguucagug gagagucugu agucauuaac acaaacucug gaagcuccac cucaagauuu       60
ucca                                                                    64

<210> SEQ ID NO 11
<211> LENGTH: 21
<212> TYPE: DNA
<213> ORGANISM: Artificial sequence
<220> FEATURE:
<223> OTHER INFORMATION: PCR primer forward

<400> SEQUENCE: 11
tacatgttcg tggtccactt c                                                 21

<210> SEQ ID NO 12
<211> LENGTH: 18
<212> TYPE: DNA
<213> ORGANISM: Artificial sequence
<220> FEATURE:
<223> OTHER INFORMATION: PCR primer reverse

<400> SEQUENCE: 12
gcagatggtg gtgagcat                                                     18
```